(12) United States Patent
Yamaya

(10) Patent No.: US 7,959,559 B2
(45) Date of Patent: Jun. 14, 2011

(54) ENDOSCOPE INSERTION ASSISTING DEVICE, ENDOSCOPE APPARATUS, MEDICAL TREATMENT DEVICE AND ENDOSCOPE INSERTION METHOD

(75) Inventor: Koji Yamaya, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 701 days.

(21) Appl. No.: 11/729,040

(22) Filed: Mar. 28, 2007

(65) Prior Publication Data

US 2007/0232853 A1 Oct. 4, 2007

(30) Foreign Application Priority Data

Mar. 29, 2006 (JP) ................................. 2006-092171
Mar. 31, 2006 (JP) ................................. 2006-100166

(51) Int. Cl.
*A61B 1/00* (2006.01)
*A61B 1/04* (2006.01)
*A61M 31/00* (2006.01)
*A61M 37/00* (2006.01)
*A61M 29/00* (2006.01)

(52) U.S. Cl. ........ 600/115; 600/116; 600/114; 600/104; 600/106; 604/95.03; 604/101.04

(58) Field of Classification Search .................. 600/104, 600/106, 114–116, 121; 604/95.03, 96.01, 604/101.02, 101.04
See application file for complete search history.

(56) References Cited

U.S. PATENT DOCUMENTS

2004/0186349 A1 * 9/2004 Ewers et al. .................. 600/114
2009/0227835 A1 * 9/2009 Terliuc .......................... 600/106

FOREIGN PATENT DOCUMENTS

| EP | 1588733 A1 | * 10/2005 |
| JP | 2000-023909 | 1/2000 |
| JP | 2004-358222 | 12/2004 |
| JP | 2005-007030 | 1/2005 |

* cited by examiner

*Primary Examiner* — Thomas J Sweet
*Assistant Examiner* — Ryan Henderson
(74) *Attorney, Agent, or Firm* — Scully, Scott, Murphy & Presser PC

(57) ABSTRACT

The present invention includes a first balloon member having a first hollow portion that allows an insertion portion of the endoscope to pass therethrough; a first transmission member that transmits an advance/retreat action performed by an operator to the first balloon member; a second balloon member having a second hollow portion that allows the insertion portion of the endoscope to pass therethrough; a second transmission member that transmits an advance/retreat action performed by an operator to the second balloon member; and a control portion that controls supply and exhaust of fluid to and from the inside of the first balloon member and the second balloon member to expand or contract the first balloon member and the second balloon member.

7 Claims, 29 Drawing Sheets

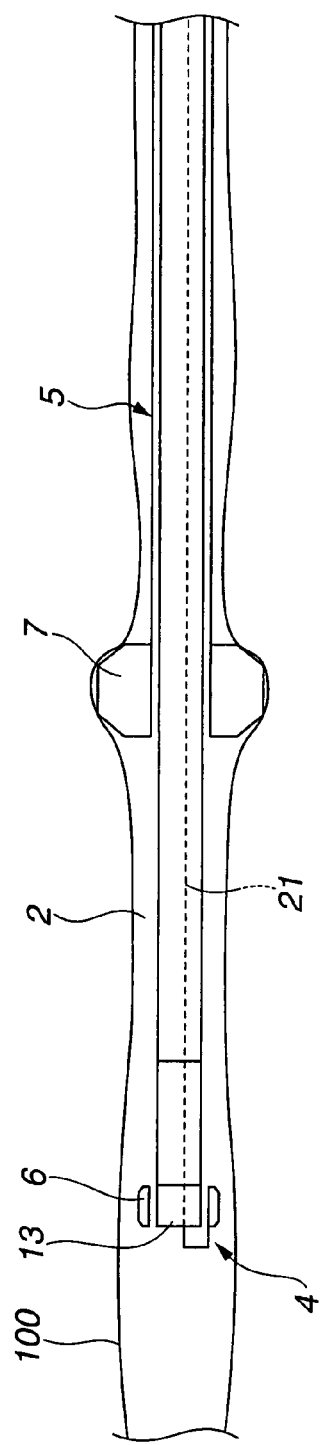
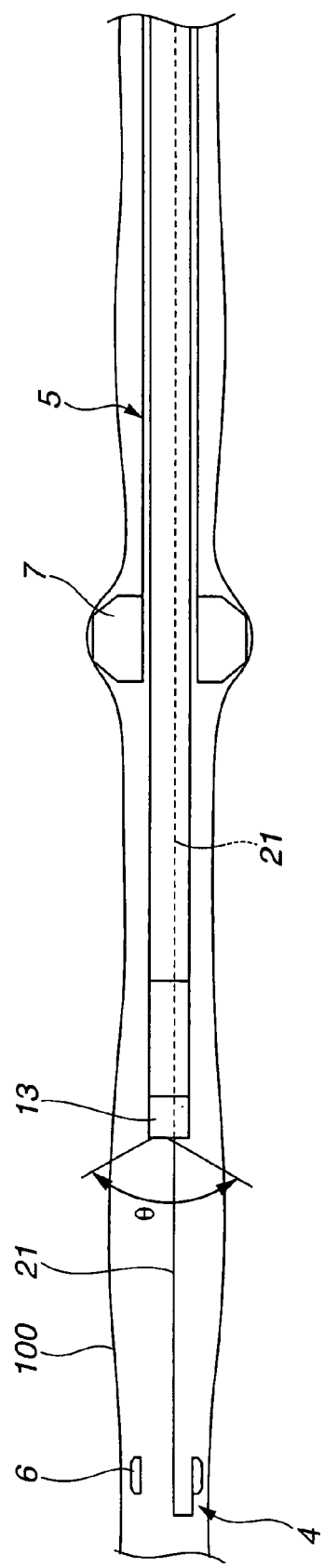

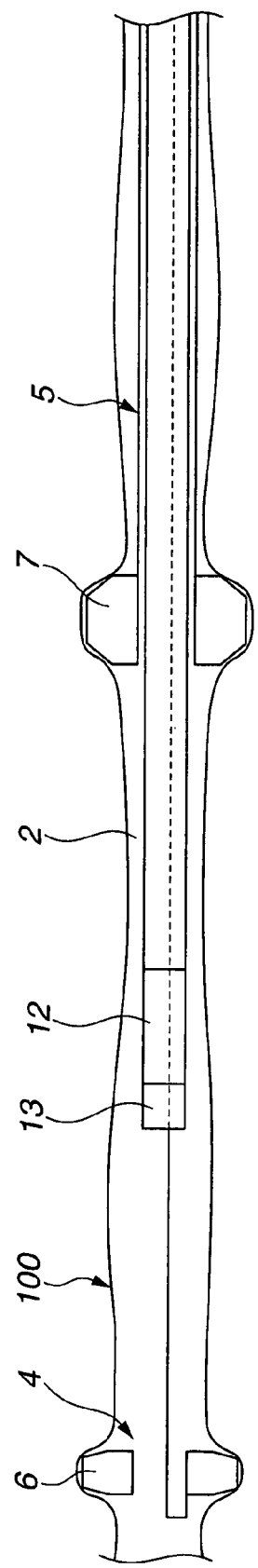
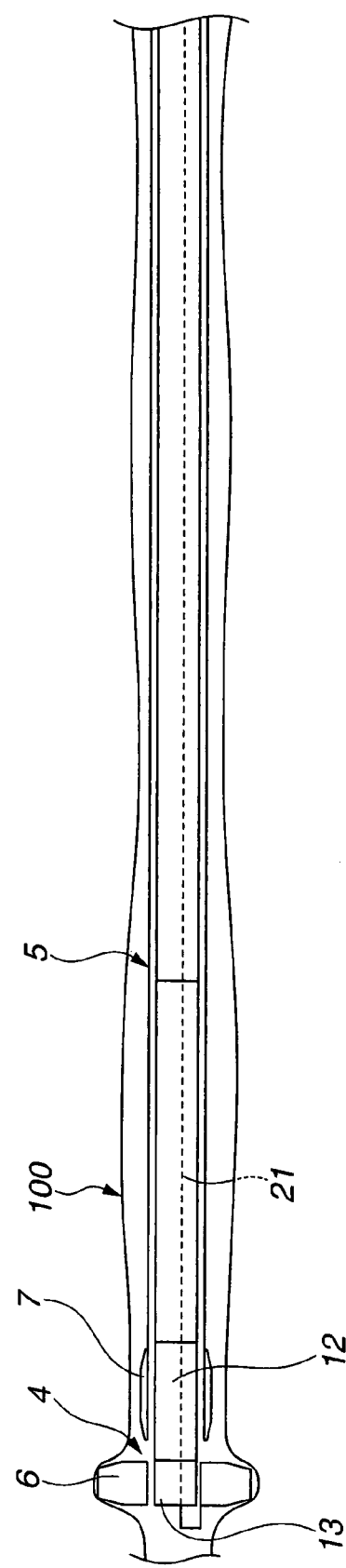

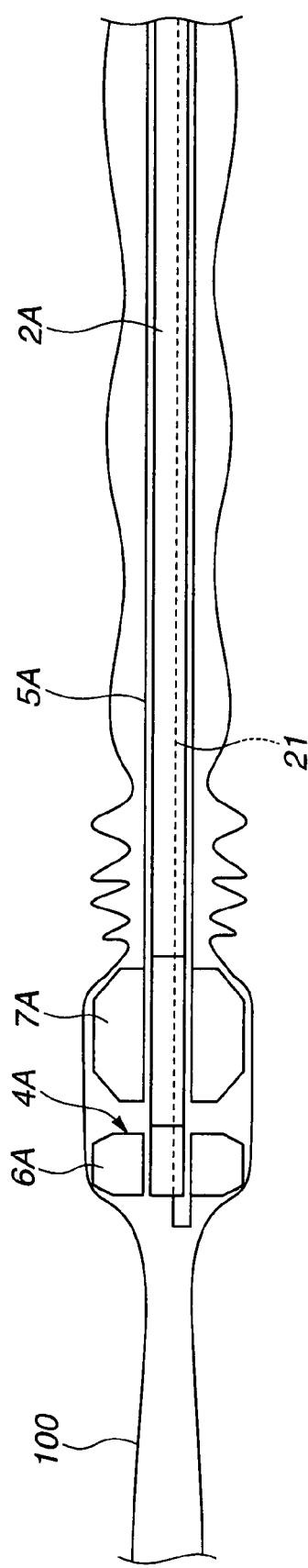
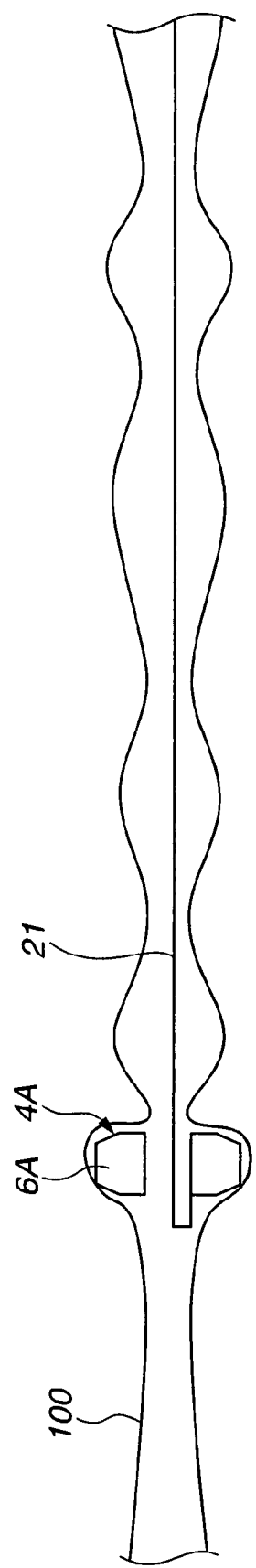
FIG.16
FIG.17

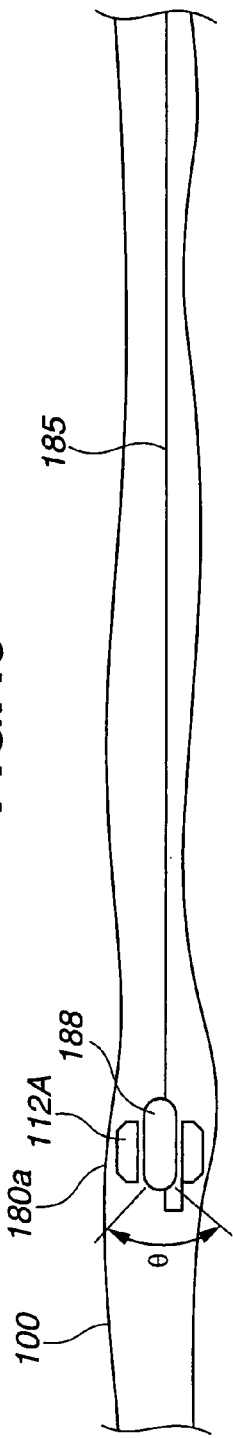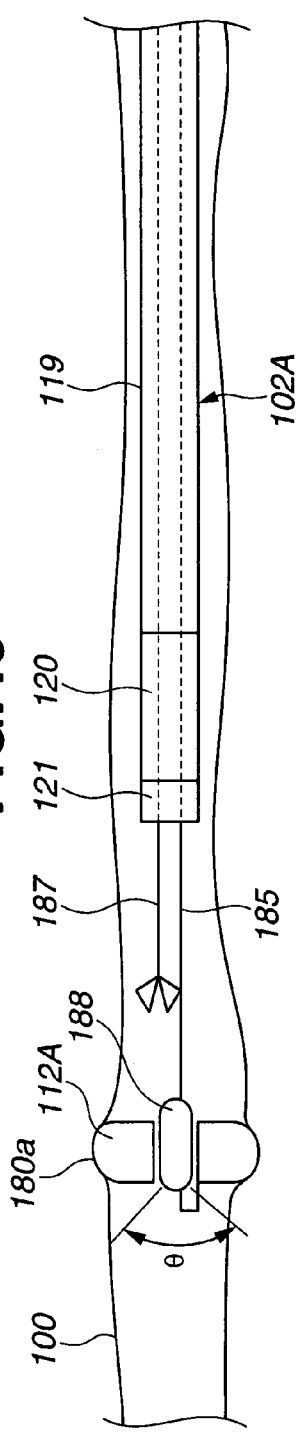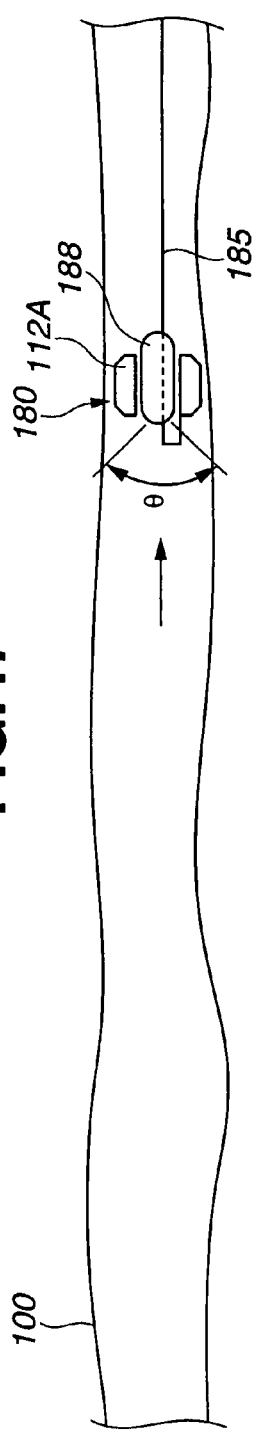

ENDOSCOPE INSERTION ASSISTING DEVICE, ENDOSCOPE APPARATUS, MEDICAL TREATMENT DEVICE AND ENDOSCOPE INSERTION METHOD

This application claims benefit of Japanese Application No. 2006-092171 filed on Mar. 29, 2006 and No. 2006-100166 filed on Mar. 31, 2006 the contents of which are incorporated by this reference.

BACKGROUND OF THE INVENTION

1. Field of the Invention

The present invention relates to an endoscope apparatus and an endoscope insertion assisting device suitable for smoothly inserting an insertion portion of an endoscope inserted into a body cavity and the like, for example, into a lumen of the large intestine or small intestine anally or orally. The present invention also relates to a medical treatment device which inserts an insertion portion of the endoscope inserted into a body cavity and the like using a balloon, for example, anally or orally into a lumen of the large intestine or small intestine or the like to observe or treat a predetermined site inside the lumen.

2. Description of the Related Art

In general, an endoscope comprises an operation unit which a technician holds to perform various operations and an insertion unit. The insertion unit comprises a flexible portion which is a long and slender tube which has flexibility and extends from the operation unit, a bending portion that is connected to the tip of the flexible portion and that can bend to the left and right or upward and downward in accordance with an operation of the operation unit, and a rigid tip component portion that is connected to the tip of the bending portion.

A technician inserts the insertion unit of this kind of endoscope into a body cavity anally, orally or nasally to perform observation and diagnosis or observation and treatment or the like at a predetermined site.

To insert the insertion unit of the endoscope into a body cavity, conventionally a method has been principally adopted in which force is exerted on the insertion unit of the endoscope from outside the body of the patient to push the insertion unit into the body cavity of the patient.

However, according to this pushing-in method, when inserting the insertion unit of an endoscope into the large intestine or small intestine anally or orally, because the intraluminal diameter of these intestines is narrow and the intestines are long and twist and turn in a complicated manner, while on the other hand the intestines are flexible and not tight, even if the insertion unit of the endoscope is pressed or moved in an advancing direction by pushing in the insertion unit of the endoscope, when the force that pushes in the endoscope is released the insertion unit is pushed back to almost its original position by the reaction force. Consequently endoscope insertion unit advances with difficulty, and since that return effect is particularly noticeable as the insertion unit reaches a deeper part of the intestine, the examination time is long and the examination is difficult when using this kind of pushing-in method, particularly when inserting the endoscope insertion unit into a deep part of the intestine.

Therefore, in view of the above described problems, endoscope insertion assisting devices have already been proposed in the prior art. For example, Japanese Patent Laid-Open No. 2000-23909 and Japanese Patent Laid-Open No. 2004-358222 disclose technologies that enable an endoscope insertion unit to be inserted into the intestinal tract of a patient without simply pushing the endoscope insertion unit into the body of the patient by applying force from outside.

The endoscope insertion assisting device disclosed in the aforementioned Japanese Patent Laid-Open No. 2000-23909 has a first balloon that is fixed at a distal end of an endoscope insertion unit and a second balloon that can be caused to protrude from the distal end of the endoscope and can be moved to a position far from or near the distal end thereof, wherein the endoscope insertion unit is pushed and advanced while retaining and releasing the intestinal tract by expanding and contracting the first and second balloons, respectively, to insert the endoscope distal end to the deep part of the intestinal tract.

The endoscope insertion assisting device disclosed in the aforementioned Japanese Patent Laid-Open No. 2004-358222 has a first balloon that is fixed at a distal end of an endoscope insertion unit and a second balloon that is fixed at a distal end of an overtube that is sheathed over the endoscope insertion unit, wherein the endoscope insertion unit is pushed and advanced while retaining and releasing the intestinal tract by expanding and contracting the first and second balloons, respectively, to insert the endoscope distal end to the deep part of the intestinal tract.

Further, an endoscope apparatus disclosed in Japanese Patent Laid-Open No. 2005-7030 is adapted to advance an endoscope insertion unit while retaining and releasing the intestinal tract to insert the endoscope distal end into the deep part of the intestinal tract by expanding and contracting a first balloon provided at the distal end of the endoscope insertion unit and a second balloon provided at a distal end of an overtube that covers the endoscope insertion unit, respectively, by controlling the supply and exhaust of a fluid using a balloon control device. The endoscope apparatus also has display means that displays the supply and exhaust state of fluid to the first balloon and the second balloon on a monitor so that the operator can ascertain the supply and exhaust state of fluid to the first balloon and the second balloon from the display contents that are displayed on the display means.

SUMMARY OF THE INVENTION

To achieve above described object, an endoscope insertion assisting device according to the present invention comprises: a first balloon member having a first hollow portion that allows an insertion portion of an endoscope inserted into a body cavity and the like to pass therethrough; a first transmission member that transmits an advance/retreat action performed by an operator to the first balloon member; a second balloon member having a second hollow portion that allows the insertion portion of the endoscope to pass therethrough; a second transmission member that transmits an advance/retreat action performed by an operator to the second balloon member; and a control portion that controls supply and exhaust of fluid to and from inside of the first balloon member and the second balloon member to expand or contract the first balloon member and the second balloon member.

And an endoscope apparatus of the present invention comprises: an endoscope comprising a long and slender insertion portion that is insertable into a body cavity, and an endoscope insertion assisting device that is constituted in combination with the endoscope; wherein, the endoscope insertion assisting device comprises: a first balloon member having a first hollow portion that allows the insertion portion to pass therethrough; a first transmission member that transmits an advance/retreat action performed by an operator to the first balloon member; a second balloon member having a second hollow portion that allows the insertion portion to pass therethrough; a second transmission member that transmits an advance/retreat action performed by an operator to the second balloon member; and a control portion that controls supply and exhaust of fluid to and from inside of the first balloon member and the second balloon member to expand or contract the first balloon member and the second balloon member.

And a medical treatment device of the present invention comprises: a supply conduit that is a conduit that is inserted inside a body cavity or inside a lumen, wherein the supply conduit is connected to a fluid supply portion that supplies or sucks a fluid, and is supplied with the fluid from the fluid supply portion or has the fluid sucked therefrom by the fluid supply portion; a balloon that is communicably connected to the supply conduit, and which can expand upon reaching a first pressure or more as a result of supply of the fluid; and an elastic member that is communicably connected to the supply conduit, and which can expand upon reaching a second pressure or more that is greater than the first pressure.

Further, an endoscope insertion method that inserts into a body cavity an endoscope apparatus of the present invention, the endoscope apparatus including: a first balloon member having a first hollow portion that allows an insertion portion of an endoscope inserted into the body cavity or the lumen to pass therethrough; a first transmission member that transmits an advance/retreat action performed by an operator to the first balloon member; a second balloon member having a second hollow portion that allows the insertion portion of the endoscope to pass therethrough; and a second transmission member that transmits an advance/retreat action performed by an operator to the second balloon member; the method comprises the steps of: expanding the second balloon member to retain the body cavity and the second transmission member by contacting the second balloon member against a body cavity wall surface; moving the insertion portion of the endoscope in an insertion direction with respect to the second transmission member that retains the body cavity; moving the first transmission member in an insertion direction with respect to the insertion portion of the endoscope that is moved; expanding the first balloon member to retain the body cavity and the first transmission member by contacting the first balloon member against a body cavity wall surface; moving the insertion portion of the endoscope towards the first balloon member that retains the body cavity; and moving the second transmission member toward the first balloon member that retains the body cavity, in a state in which the second balloon is contracted.

The above and other objects, features and advantages of the invention will become more clearly understood from the following description referring to the accompanying drawings.

BRIEF DESCRIPTION OF THE DRAWINGS

FIG. 6 is a view showing a state in which, after expanding the second balloon from the state shown in FIG. 5 to retain the intestinal tract, the endoscope is pushed in using the maximum stroke;

FIG. 7 is a view showing a state in which, in the state shown in FIG. 6, a shaft is pushed in to insert the first balloon into a deep part of the intestinal tract;

FIG. 8 is a view showing a state in which, in the state shown in FIG. 7, the first balloon is expanded to retain the intestinal tract;

FIG. 9 is a view showing a state in which, from the state shown in FIG. 8, a second balloon 7 is contracted and a second endoscope insertion assisting device and the insertion unit are advanced to the deep part of the intestinal tract;

FIG. 16 is a view showing a state in which the endoscope according to the second modification example and the first and second endoscope insertion assisting device are inserted into the intestinal tract in a combined state;

FIG. 17 is a view showing a state in which the endoscope and the second endoscope insertion assisting device are extracted from the state shown in FIG. 16;

FIG. 28 is an explanatory drawing that shows a state in which air is supplied to the supply line from the balloon control device in a state in which an expansion action of the first balloon is restricted from outside by a body wall or the like;

FIG. 45 is a view illustrating a second modification example of the fifth embodiment, and shows a state in which a first balloon is inserted into a deep part of the intestinal tract while performing observation with a capsule endoscope;

FIG. 46 is a view showing a state in which, from the state shown in FIG. 45, the first balloon is expanded to insert an endoscope, and a treatment instrument is also inserted; and FIG. 47 is a view showing a state in which, after completing treatment at the deep part of the intestinal tract, the endoscope is withdrawn to recover the capsule endoscope.

DETAILED DESCRIPTION OF THE PREFERRED EMBODIMENTS

Hereunder, embodiments of the present invention will be described with reference to the drawings.

First Embodiment

Figure 1:
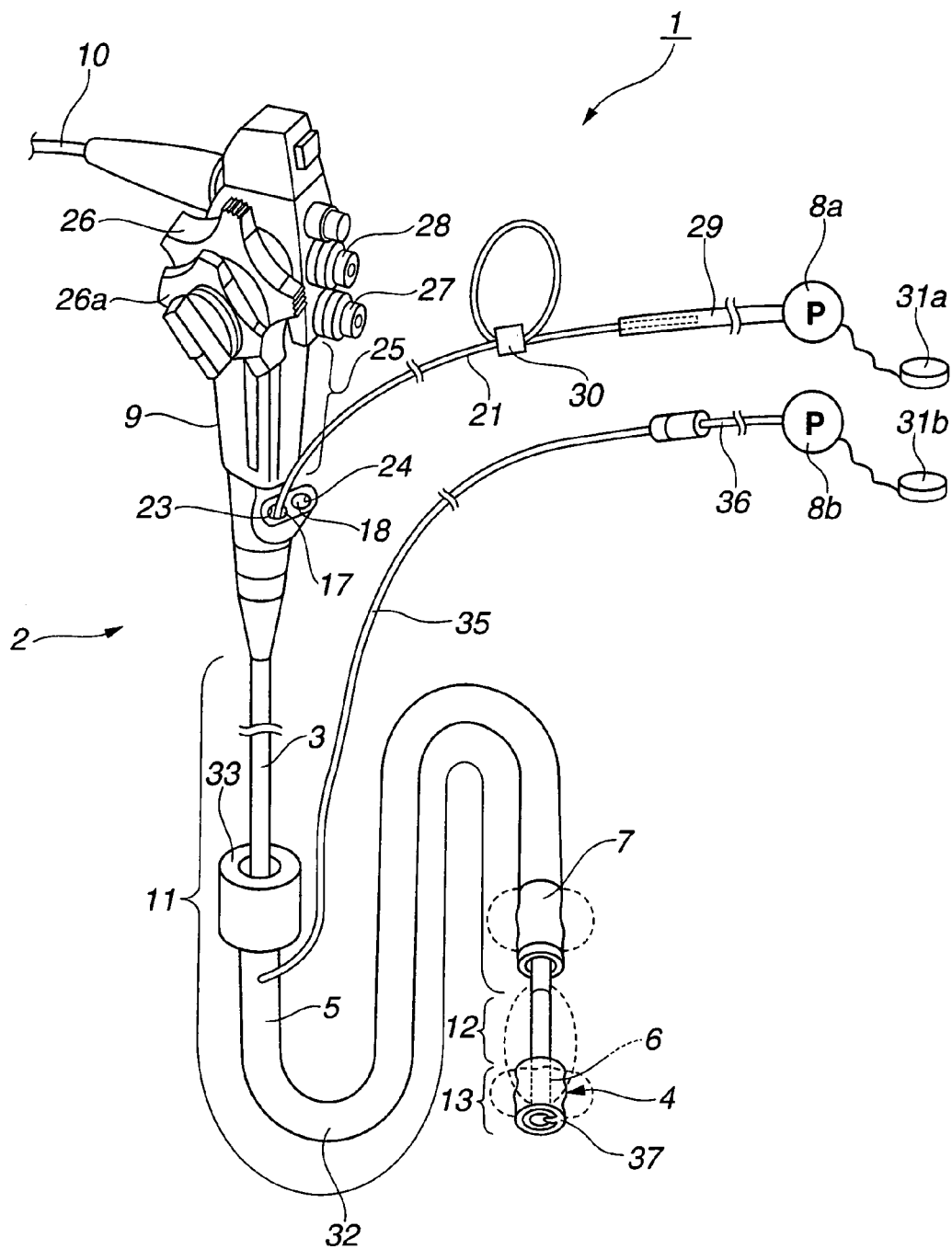
FIG. 1 is a configuration diagram that shows the overall configuration of an endoscope apparatus according to a first embodiment of the present invention.
Figure 2:
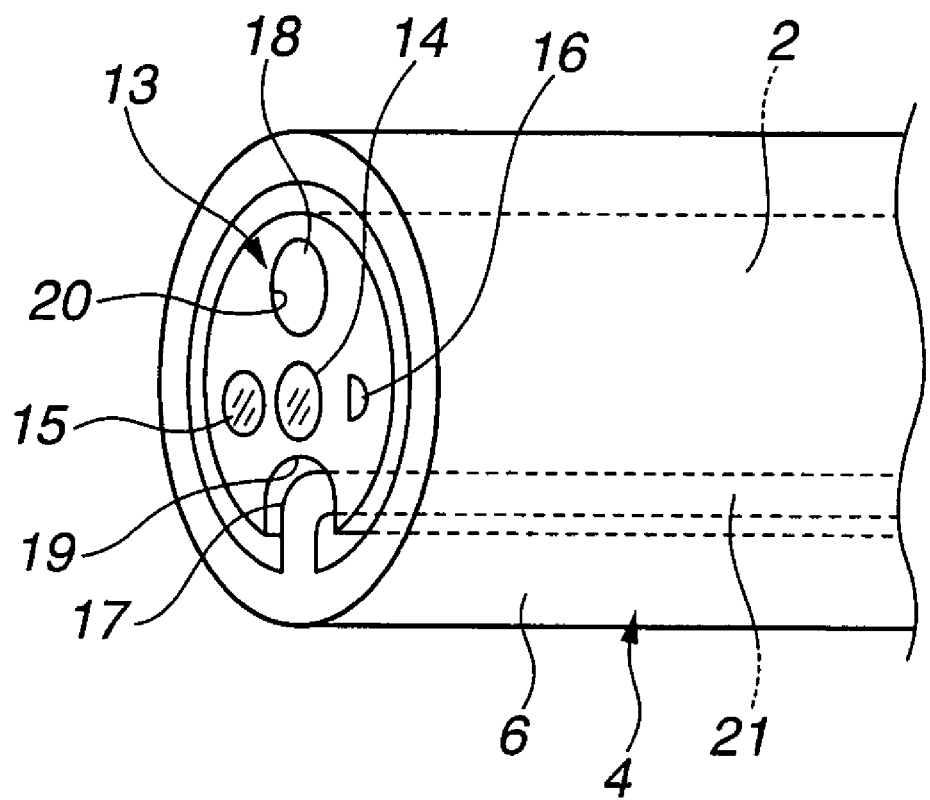
FIG. 2 is an oblique perspective view that shows a portion of the distal end of the endoscope in a state in which the endoscope is provided with a first endoscope insertion assisting device that can be freely advanced or pulled back in a state in which it is pulled in to the side nearest the technician's hands.
Figure 3:
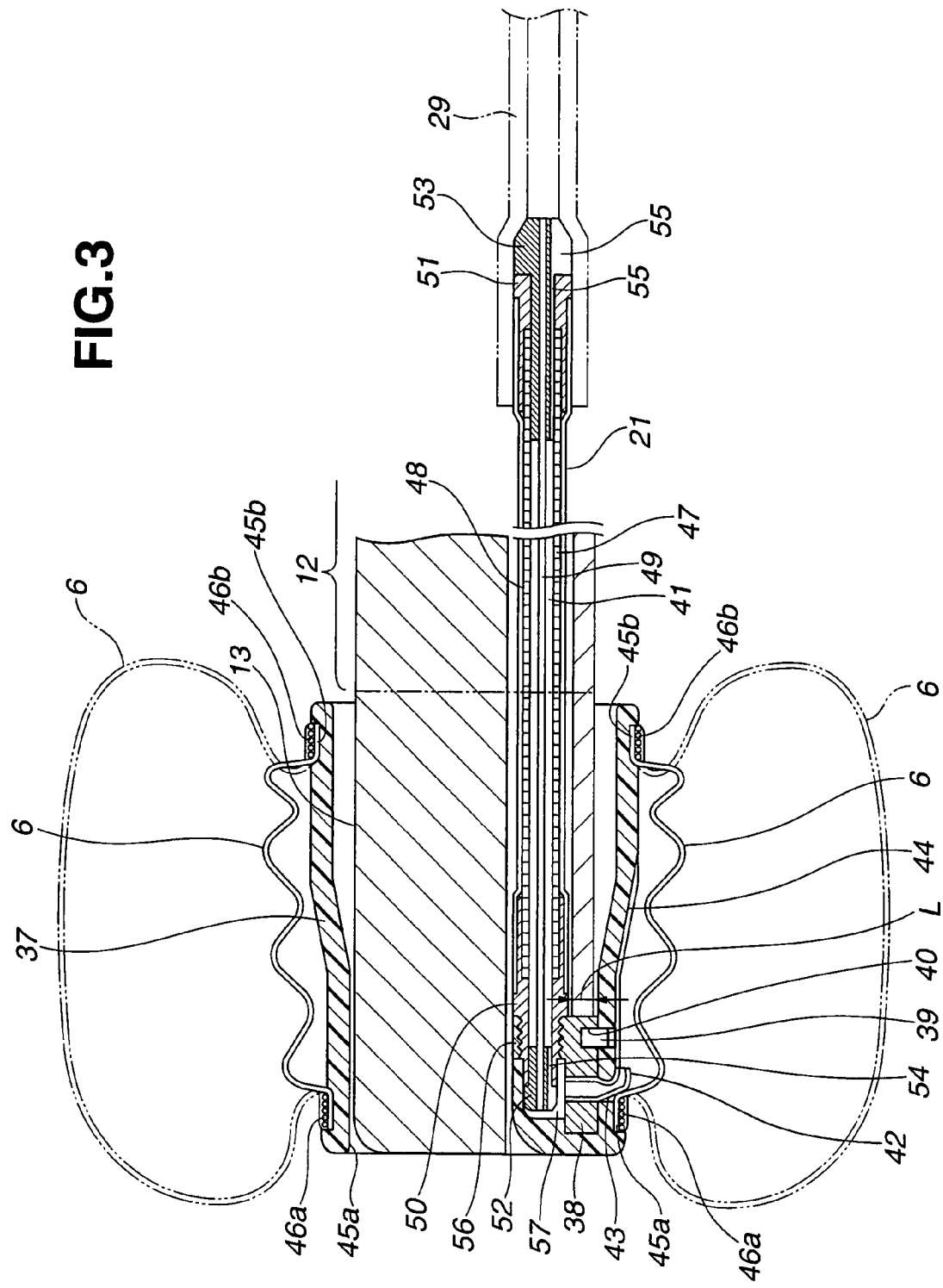
FIG. 3 is a sectional view in the longitudinal direction of the first endoscope insertion assisting device shown in FIG. 1.

FIG. 1 to FIG. 13 relate to a first embodiment of the present invention. FIG. 1 is a configuration diagram that shows the overall configuration of an endoscope apparatus, FIG. 2 is an oblique perspective view that shows a portion of the distal end of the endoscope in a state in which the endoscope is provided with a first endoscope insertion assisting device that can be freely advanced or pulled back in a state in which it is pulled in to the side nearest the technician's hands; FIG. 3 is a sectional view in the longitudinal direction of the first endoscope insertion assisting device shown in FIG. 1, FIG. 4 to FIG. 12 are explanatory drawings for describing a state in which the intestinal tract is drawn in while expanding and contracting a first balloon of the first endoscope insertion assisting device and a second balloon of a second endoscope insertion assisting device to advance the distal end of the endoscope to a deep part of the intestinal tract, and FIG. 13 is a flowchart for describing the operations according to the present embodiment which shows the respective states from FIG. 4 to FIG. 12 in a time series.

As shown in FIG. 1, an endoscope apparatus 1 according to the first embodiment of the present invention comprises an endoscope 2, a first endoscope insertion assisting device 4, a second endoscope insertion assisting device 5, a first balloon 6, a second balloon 7, and balloon control devices 8a and 8b. The first balloon 6 comprises one portion of a first balloon member, and the second balloon 7 comprises one portion of a second balloon member.

The endoscope 2 is inserted into a body cavity (lumen) or the like and used for endoscopy. The first endoscope insertion assisting device 4 is provided in a freely movable condition forward of the distal side of the insertion unit 3 of the endoscope 2. The second endoscope insertion assisting device 5 is mounted in a freely moveable condition across the entire length of the insertion unit 3 of the endoscope 2. The first balloon 6 is provided on the first endoscope insertion assisting device 4, and the second balloon 7 is provided on the second endoscope insertion assisting device 5. The balloon control device 8a performs control to supply fluid to the first balloon 6 or to exhaust fluid therefrom by suction. The balloon control device 8b performs control to supply fluid to the second balloon 7 or to exhaust fluid therefrom by suction.

The endoscope 2 has a long and slender insertion unit 3 which is an insertion portion that is inserted into a body cavity or the like, an operation unit 9 provided at a proximal of the insertion unit 3, and a universal cable 10 that extends from a side portion of the operation unit 9. An unshown connector is provided at an end of the universal cable 10. The universal cable 10 is detachably connected to an unshown light source device and signal processing device by the unshown connector.

The insertion unit 3 comprises a flexible tube portion 11 that is long and slender and has flexibility, a bendable bending portion 12 that is connected to the tip of the flexible tube portion 11, and a rigid distal end 13 that is connected to the tip of this bending portion 12.

FIG. 1 shows a state at a time when the endoscope 2 is to be inserted into a body cavity. According to the present embodiment, as shown in FIG. 1, the first endoscope insertion assisting device 4 and the second endoscope insertion assisting device 5 cover the insertion unit 3 in a moveable condition. The specific configuration of the first endoscope insertion assisting device 4 and the second endoscope insertion assisting device 5 will be described later.

FIG. 2 shows a magnified view of the distal end 13 to which the first endoscope insertion assisting device 4 is attached.

As shown in FIG. 2, at the distal end 13, for example, an observation window 14 is provided adjacent to the center of the front end surface, and on the two sides thereof are respectively provided an illumination window 15 and an air supply and water supply nozzle 16.

A light guide (not shown) that transmits an illumination light passes through the inner side of an illumination lens that is attached to the illumination window 15. This light guide (not shown) passes through the inside of the insertion unit 3 and the like to be detachably connected to a light guide connector of the light source device. An illumination light that is generated at the light source device is transmitted by the light guide and emitted from the illumination window 15 to thereby illuminate the inside of the body cavity as the field of view range (denoted by θ in FIG. 7) of the observation window 14.

An unshown objective lens is provided in the observation window 14. For example, a CCD (unshown) is disposed as an image pickup device at an image formation position of the objective lens. The CCD (unshown) performs photoelectric conversion of an optical image of inside the body cavity that is formed on the image pickup surface.

Further, although not shown in the figure, the CCD is connected to a signal cable and the signal cable is passed through the inside of the insertion unit 3 and the like to be electrically connected to the signal processing device. The signal processing device performs signal processing of image pickup signals that were picked up by the CCD to generate video signals and output the video signals to a monitor, to thereby display the optical images of inside the body cavity that were picked up by the CCD on a display screen of the monitor.

Further, as shown in FIG. 2, with respect to the direction in which the air supply and water supply nozzle 16, the observation window 14 and the illumination window 15 are aligned, for example, on the two sides in a substantially orthogonal direction thereto, are provided a first channel opening 19 and a second channel opening 20 that respectively form the openings for a first channel 17 and a second channel 18 provided inside the insertion unit 3.

The first channel opening 19 opens from the front surface of the distal end 13 to the side surface thereof. A shaft (shaft element) 21 that constitutes the first endoscope insertion assisting device 4 passes through the first channel opening 19. The shaft 21 is a first transmission member that transmits an advance/retreat action performed by an operator, and at the same time, constitutes a first fluid supply and exhaust line that supplies and drains fluid to and from the inside of the first balloon 6 comprising the first endoscope insertion assisting device 4.

As shown in FIG. 1, the first channel 17 and the second channel 18 that are provided along the longitudinal direction of the above described insertion unit 3 respectively connect to a first channel insertion port 23 and a second channel insertion port 24 that are arranged adjacent to the front end of the operation unit 9 shown in FIG. 1.

Also, as shown in FIG. 1, a grip portion 25 is provided at a section approaching the front end of the operation unit 9. Bending operation knobs 26 and 26a are provided at a side that is further toward the rear end of the operation unit 9 than the grip portion 25. According to this configuration, a technician can grip the grip portion 25 to operate the bending operation knobs 26 and 26a that are provided on the operation unit 9 and the like.

That is, since the bending operation knobs 26 and 26a are provided on the operation unit 9 at a side that is further toward the rear end thereof than the grip portion 25, a technician can grip the grip portion 25 and rotationally operate the bending operation knobs 26 and 26a with the fingers of one hand, and can bend the bending portion 12 in an arbitrary direction upward and downward and left and right by that rotational operation.

The bending portion 12 comprises a plurality of annular bending elements that are rotatably connected in the longitudinal direction of the bending portion 12, and these bending elements comprising the bending portion 12 can be bent by a rotational operation of the bending operation knobs 26 and 26a via a bending wire.

As shown in FIG. 1, on a surface adjoining the surface on which the bending operation knobs 26 and 26a are provided on the operation unit 9 are provided an air supply and water supply button 27 and a suction button 28 for performing a suction operation. According to this configuration, by operating the air supply and water supply button 27, a technician can supply air or supply water from the air supply and water supply nozzle 16 that is provided at the distal end 13.

By operating the suction button 28, a technician can carry out an operation to suck liquid or another type of fluid through the second channel 18 of the distal end 13 from the second channel opening 20 thereof.

The second channel 18 can be used as a conduit in which to pass through a treatment instrument, and can also be used as a suction line that sucks a fluid. Therefore, in the vicinity of the front end inside the operation unit 9, the rear end side of the second channel 18 branches into a conduit that connects to the second channel insertion port 24 and a suction line (not shown) that extends to the rear end side of the operation unit 9.

When a treatment instrument is inserted from the second channel insertion port 24, the distal side of the inserted treatment instrument protrudes from the second channel opening 20 of the distal end 13 through the internal second channel 18 to thereby enable a biopsy and other kinds of treatment to be carried out under observation from the observation window 14.

According to the present embodiment, the shaft 21 constituting the first endoscope insertion assisting device 4 is inserted from the side of the first channel opening 19 and guided to outside through the first channel insertion port 23 of the operation unit 9. Further, the balloon control device 8a that is a control portion (first fluid supply and exhaust portion) is connected as control means (more specifically, first fluid supply and exhaust means) to a proximal portion of the shaft 21 that is guided to outside from the first channel insertion port 23 through a first connection tube 29.

The shaft 21 is configured to have a sufficient length from the first channel insertion port 23 to the first connection tube 29. In this case, the shaft 21 is configured such that a loop of an arbitrary size or loops of an arbitrary number of windings can be formed in the shaft 21, for example, using a retaining member 30 such as a clip as shown in FIG. 1. Thus, by forming a loop in the shaft 21, it is possible to arbitrarily adjust the rigidity of the shaft 21 (the inner structure of the shaft 21 will be described later).

By gripping a portion (first operation unit) of the shaft 21 that extends from the operation unit 9 to perform an advance/retreat action, a technician or an assistant can freely position the first balloon 6 that is provided at the tip of the first endoscope insertion assisting device 4 forward or rearward of the field of view.

A first foot switch 31a that is an instructing unit is connected as instructing means to the balloon control device 8a that is connected to the proximal side of the shaft 21. The balloon control device 8a performs supply and exhaust control of fluid to the first balloon 6 of the first endoscope insertion assisting device 4 based on instruction operations by the first foot switch 31a. It is thereby possible to freely expand and contract the first balloon 6.

Further, as shown in FIG. 1, the second endoscope insertion assisting device 5 comprises a hollow shaped, flexible tube element 32, a second balloon 7 that is provided on the distal side of the tube element 32, and an at-hand grip portion 33 (second operation unit) provided on the proximal side of the tube element 32.

The inner diameter that is formed across the entire length of the second endoscope insertion assisting device 5 has a diameter that is slightly larger than the outer diameter of the insertion unit 3 of the endoscope 2. In this connection, the tube element 32 constitutes a second transmission member, and the at-hand grip portion 33 constitutes a second operation unit.

The tube element 32 is formed of, for example, a biocompatible material such as silicon and, for example, is transparent. A hydrophilic lubricant coating, for example, is applied on at least the inner surface of the tube element 32. This configuration ensures that the insertion unit 3 of the endoscope 2 has favorable properties with respect to its ability to pass through the second endoscope insertion assisting device 5.

The second balloon 7 is provided on the distal side of the second endoscope insertion assisting device 5. The second balloon 7 is formed, for example, using an elastic material such as rubber, and is fitted onto and covers the outer circumference of the tube element 32. The two ends of the second balloon 7 are hermetically adherently fixed to the tube element 32.

A second fluid supply and exhaust line (not shown) that communicates from the vicinity of the at-hand grip portion 33 to the inner surface of the second balloon 22 is also formed in the tube element 32. The second fluid supply and exhaust line (not shown) has a second fluid supply and exhaust connection tube 35 that is connected to the side of the tube element 32 nearer the technician's hands, and the second fluid supply and exhaust line extends from the tube element 32 by means of the second fluid supply and exhaust connection tube 35.

The balloon control device 8b that is a control portion is connected as control means to the proximal portion of the second fluid supply and exhaust connection tube 35 via a second connection tube 36.

According to the present embodiment, with respect to the second endoscope insertion assisting device 5, the insertion unit 3 of the endoscope 2 is inserted and mounted through the opening in the at-hand grip portion 33 prior to the first endoscope insertion assisting device 4. Further, the dimensions of the inner and outer diameters of the distal end of the second endoscope insertion assisting device 5 are formed so as contact the end of a balloon retaining member 37 of the first endoscope insertion assisting device 4.

A second foot switch 31b that is an instructing unit is also connected as instructing means to the balloon control device 8b. The balloon control device 8b performs supply and exhaust control of fluid to the second balloon 7 of the second endoscope insertion assisting device 5 based on instruction operations by the second foot switch 31b. It is thereby possible to freely expand and contract the second balloon 7.

In this connection, the balloon control device 8b, the second fluid supply and exhaust line, the second fluid supply and exhaust connection tube 35 and the second connection tube 36 constitute second fluid supply and exhaust means as a second fluid supply and exhaust portion.

Next, the configuration of the first endoscope insertion assisting device 4 shown in FIG. 1 will be described with reference to FIG. 3. The first balloon 6 that is represented by a chain double-dashed line in FIG. 3 illustrates one example of the shape of the first balloon 6 when expanded.

As shown in FIG. 3, the first endoscope insertion assisting device 4 is mounted so as to sheathe the distal end 13 of the insertion unit 3. The first endoscope insertion assisting device 4 mainly comprises the first balloon 6, the balloon retaining member 37 and the shaft 21.

The first balloon 6 is an expanding/contracting member (balloon member) that is formed in a hollow shape and expands and contracts. The balloon retaining member 37 retains the first balloon 6. The shaft 21 constitutes an supply and exhaust line through which a fluid such as air for expanding/contracting the first balloon 6 is passed, and also freely moves the first balloon 6 and the balloon retaining member 37 forward or backward.

The first endoscope insertion assisting device 4 may be a disposable article that is discarded after one use, or may be a reusable article that is reused after being washed, disinfected and sterilized after use.

The balloon retaining member 37 is connected and fixed to the distal end of the shaft 21 by a connecting member 38. The balloon retaining member 37 fixes and retains the first balloon 6 so as to be covered by the first balloon 6. In this connection, the balloon retaining member 37 and the connecting member 38 constitute one portion of the first balloon member.

In this case, balloon fixing portions 45a and 45b are provided on the outer peripheral surface at the front side and rear side of the balloon retaining member 37. Two ends of the first balloon 6 are adherently fixed in a hermetical condition to the balloon fixing portions 45a and 45b.

The balloon retaining member 37 is formed in a hollow shape such that it can cover the distal end 13 of the endoscope 2 from the distal side, and is formed using resin member that has electrical insulation properties, for example, a fluorocarbon resin such as Teflon®.

On the outer peripheral surface of the balloon retaining member 37 are provided a hole portion 40 in which a fixing pin 39 is fixed, a hole portion 43 for fixing a supply and exhaust nozzle 42 that communicates with a first fluid supply and exhaust line 41 inside the shaft 21, and a balloon adherence prevention groove 44 that is provided at the front side of the opening of the supply and exhaust nozzle 42.

The hole portion 40 and the hole portion 43 are formed from the top of the outer peripheral surface of the balloon retaining member 37 to the internal connecting member 38. Fitting the fixing pin 39 into the hole portion 43 connects the balloon retaining member 37 and the connecting member 38 in a fixed condition.

The balloon adherence prevention groove 44 constitutes one part of a prevention mechanism for ensuring that, even in a state in which the first balloon 6 is completely contracted by the supply and exhaust of fluid from the supply and exhaust nozzle 42, the first balloon 6 does not adhere to and block the opening of the supply and exhaust nozzle 42.

The first balloon 6 that is expanded and contracted by the supply and exhaust of fluid is formed in the shape of a hollow bag using a member having contraction and expansion properties, for example, latex. In this case, in a contracted state the first balloon 6 forms a substantially cylindrical shape, and the inner peripheral surface side of the cylinder is retained by the balloon retaining member 37, such that it is detachably mounted on the outer peripheral surface adjacent to the distal end 13.

In this connection, a configuration may be adopted in which the first balloon 6 is detachably mounted on the outer peripheral surface adjacent to the distal end 13 of the insertion unit 3, without using the balloon retaining member 37. In this case, a configuration may be adopted in which a cylindrical and hollow inner peripheral surface is formed so that, when the first balloon 6 is contracted, it is easy to detachably mount the first balloon 6 onto the outer peripheral surface adjacent to the distal end 13 of the insertion unit 3.

After the first balloon 6 is covered with the balloon retaining member 37, the two ends that correspond to the balloon fixing portions 45a and 45b are hermetically adhered by bobbin winder portions 46a and 46b that adhere, for example, using bobbin winding and an adhesive.

The bobbin winder portion 46a on the forward side adherently fixes the first balloon 6 to the balloon fixing portion 45a and, at the same time, since it is formed as far as the vicinity of the supply and exhaust nozzle 42, it also has a function to prevent the supply and exhaust nozzle 42 from slipping out from the hole portion 43.

The first balloon 6 is expanded and contracted by fluid that is supplied and exhausted through the supply and exhaust nozzle 42. According to the present embodiment, a configuration is adopted in which the distal end 13 of the endoscope 2 is sheathed by the balloon retaining member 37 that is thicker than the distal end 13. It is therefore possible to construct the first balloon 6 using a large balloon member with a thick diameter that has high retentivity with respect to the intestinal tract.

As shown in FIG. 3, the shaft 21 that is connected and fixed to the balloon retaining member 37 by the connecting member 38 comprises a long and flexible coil member 47, an outer skin member 48 that covers the entire length of the coil member 47 and has electrical insulating properties, a wire 49 disposed on the inner side of the coil member 47, and the first fluid supply and exhaust line 41 that is provided along the entire length of the inside of the coil member 47.

The outer skin member 48 is formed, for example, with a fluorocarbon resin with good slipping properties. The coil member 47 is formed, for example, by winding a stainless wire having a quadrangular sectional form so as to adhere.

At the two ends of the coil member 47, a first mouthpiece member 50 and a second mouthpiece member 51 are fixed, for example, with an adhesive or the like. A wire 49 passes through the inner side of the coil member 47. At the two ends of the wire 49, a first terminal member 52 and a second terminal member 53 are fixed, for example, with an adhesive or the like. At one portion on the outer peripheral surface between the first terminal member 52 and the second terminal member 53 are respectively formed a first groove 54 and a second groove 55 that constitute one part of the first fluid supply and exhaust line 41.

The outer skin member 48 is configured so as to sheathe the coil member 47 after the wire 49 passes through and is fixed therein. The two ends of the coil member 47 are adherently fixed in a hermetical condition on the first mouthpiece member 50 and the second mouthpiece member 51.

A threaded portion 56 is formed at the front side of the first mouthpiece member 50. By fitting together the threaded portion 56 and a threaded portion that is formed at a corresponding position of the connecting member 38, the shaft 21 can be hermetically fixed to the connecting member 38.

As long as the shaft 21 has flexibility, the material and structure thereof are not limited and, for example, a coil or the like that is formed using a stainless steel material may be used as a substitute member thereof. In addition to the shaft 21, the coil member 47, the wire 49 and the like constitute the first transmission member, and the shaft 21 and the retaining member 30 (see FIG. 1) and the like constitute the first operation unit. Further, the balloon control device 8a, the first fluid supply and exhaust line 41 and the first connection tube 29 constitute first fluid supply and exhaust means as the first fluid supply and exhaust portion.

Next, the procedures for assembling the first endoscope insertion assisting device 4 will be described. According to the present embodiment, a unit in a state in which the connecting member 38 is fixed to the shaft 21 is inserted from the rear end side of the balloon retaining member 37 to adherently fix the connecting member 38 and the balloon retaining member 37 in a hermetical condition, and further, the fixing pin 39 and the supply and exhaust nozzle are inserted and fixed from the side surface of the balloon retaining member 37.

As a result, even if an operation is performed to advance or retreat the shaft 21 in an intense manner, the operation to advance or retreat the shaft 21 can be performed smoothly without the shaft 21 and the balloon retaining member 37 coming apart.

Finally, the first balloon 6 is fixed and retained on the balloon retaining member 37 so that the first balloon 6 covers the balloon retaining member 37. Thereafter, the first connection tube 29 that extends from the balloon control device 8a is spread over and connected to the rear end portion of the shaft 21, as shown in FIG. 3, to form the first fluid supply and exhaust line 41.

More specifically, fluid that is subjected to supply control by the balloon control device 8a is supplied to or exhausted from the internal space of the first balloon 6 by the supply and exhaust nozzle 42 via a space between the second groove 55, coil member 47 and wire 49 constituting the first fluid supply and exhaust line 41 and via the first groove 54 and an internal space 57 of the balloon retaining member 37.

The balloon control device 8a controls the supply and exhaust of fluid from and to the first balloon 6 of the first endoscope insertion assisting device 4 based on instruction operations by the first foot switch 31a. By operating the first foot switch 31a, a technician can freely implement an operation from the balloon control device 8a to supply a fluid such as air via the first fluid supply and exhaust line 41 to the internal space of the first balloon 6 to expand the first balloon 6, or to suck or exhaust the fluid to contract the first balloon 6.

The balloon control device 8b controls the supply and exhaust of fluid from and to the second balloon 7 of the second endoscope insertion assisting device 5 based on instruction operations by the second foot switch 31b. By operating the second foot switch 31b, a technician can freely implement an operation from the balloon control device 8b to supply a fluid such as air via the second fluid supply and exhaust line 34 to the internal space of the second balloon 7 to expand the second balloon 7, or to suck or exhaust the fluid to contract the second balloon 7.

In the endoscope apparatus 1 having the above described configuration, an observation window 14 is provided in the distal end face of the endoscope 2. When performing observation from the observation window 14, an operation to insert the insertion unit 3 of the endoscope apparatus 1 to a deep part within a body cavity can be performed smoothly and in a short time by moving the first balloon 6 forward of the distal end 13 and the like using the first balloon 6 and the second balloon 7 as described hereunder.

That is, since the endoscope apparatus 1 according to the present embodiment has the first balloon 6, the first endoscope insertion assisting device 4 that can pass through the insertion unit 3 of the endoscope 2, the second balloon 7, and the second endoscope insertion assisting device 5 that can pass through the insertion unit 3 of the endoscope 2, a moving distance (stroke) according to one progression of the first balloon 6 can be increased. More specifically, by using the second balloon 7 of the second endoscope insertion assisting device 5, it becomes easy to perform an operation to assist insertion of the endoscope, as the first balloon 6 can be moved with a large stroke to the forward side that can be captured within the range of the field of view of the endoscope 2 as described hereunder.

Further, by mounting the first balloon 6 on the outer peripheral surface adjacent to the distal end 13 of the insertion unit 3, it is possible to mount a large-sized first balloon 6. Thus, when the first balloon 6 is expanded using a fluid, the intestinal tract is retained with a large retention force, so the endoscope 2 can be surely moved to the forward side.

The operations when performing endoscopy after inserting the endoscope 2 according to the present embodiment that has this configuration into a body cavity will be described with reference to FIGS. 4 to 13.

Figure 4:
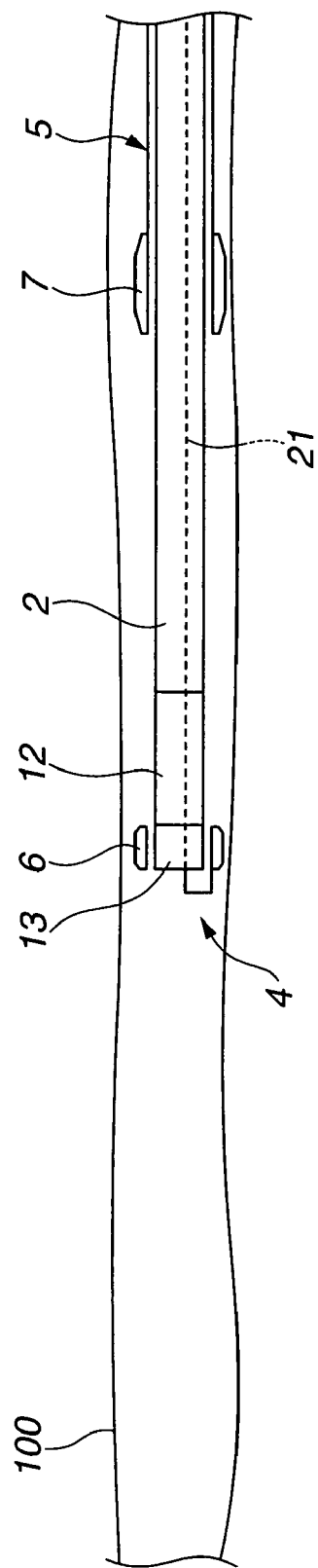
FIG. 4 is a view showing a state in which the endoscope is inserted and advanced by only the advance/retreat of the endoscope in a state in which a first and a second balloon are contracted.
Figure 5:
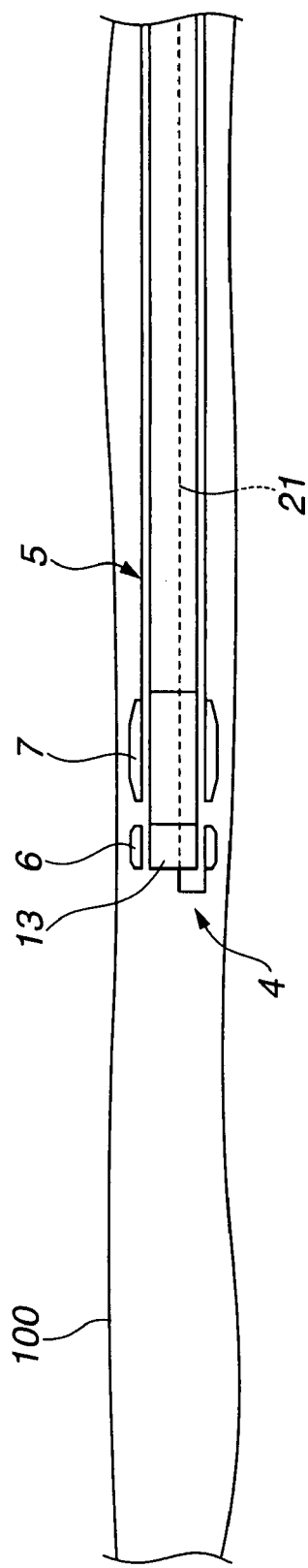
FIG. 5 is a view showing a state in which the second balloon is moved toward the distal end of the endoscope from the state shown in FIG. 4.
Figure 10:
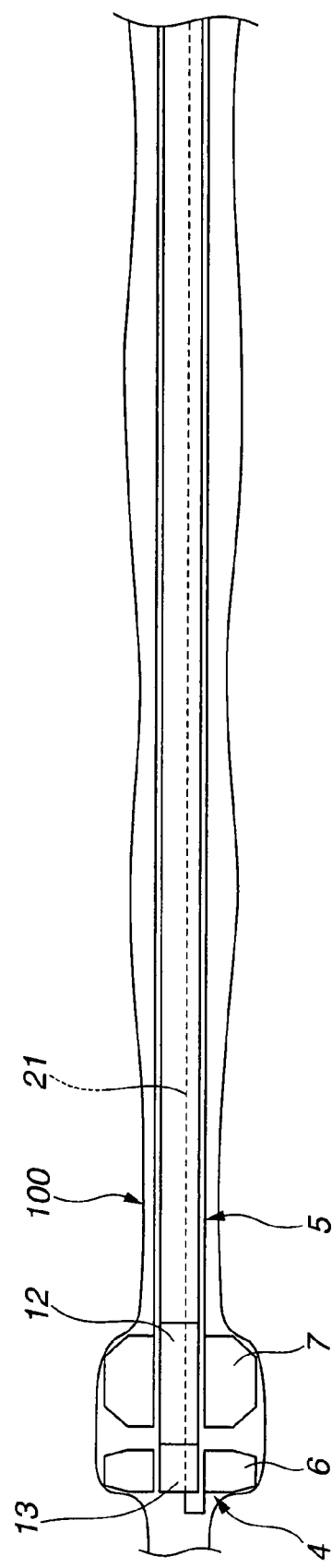
FIG. 10 is a view showing a state in which, in the state shown in FIG. 9, the second balloon is expanded such that the intestinal tract is securely retained by the first and second balloons.
Figure 11:
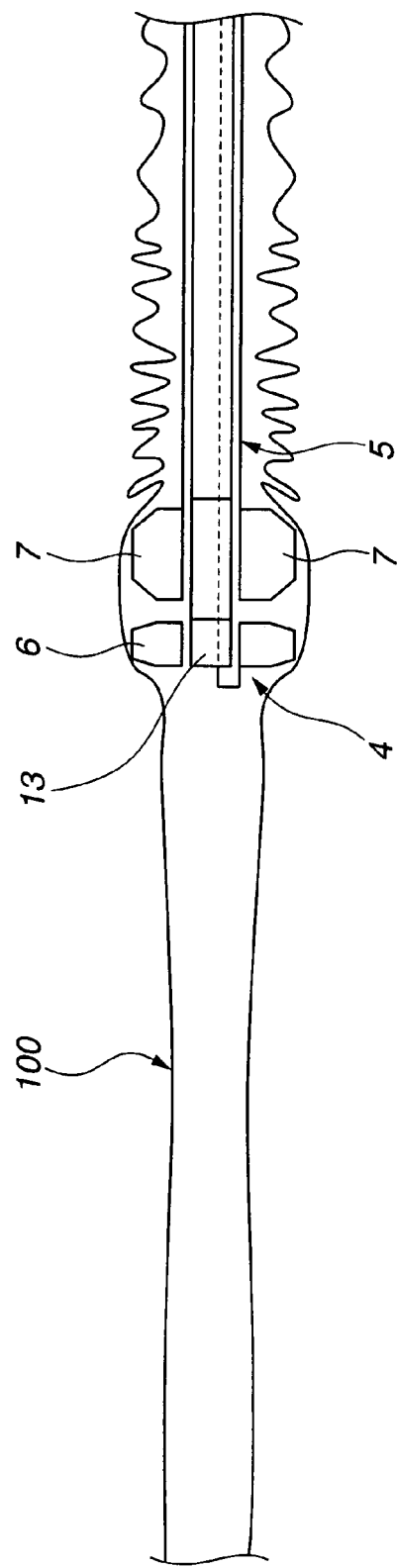
FIG. 11 is a view showing a state in which, in the state shown in FIG. 10, an operation is performed to pull in the first and second endoscope insertion assisting devices and the insertion unit to draw in the intestinal tract.
Figure 12:
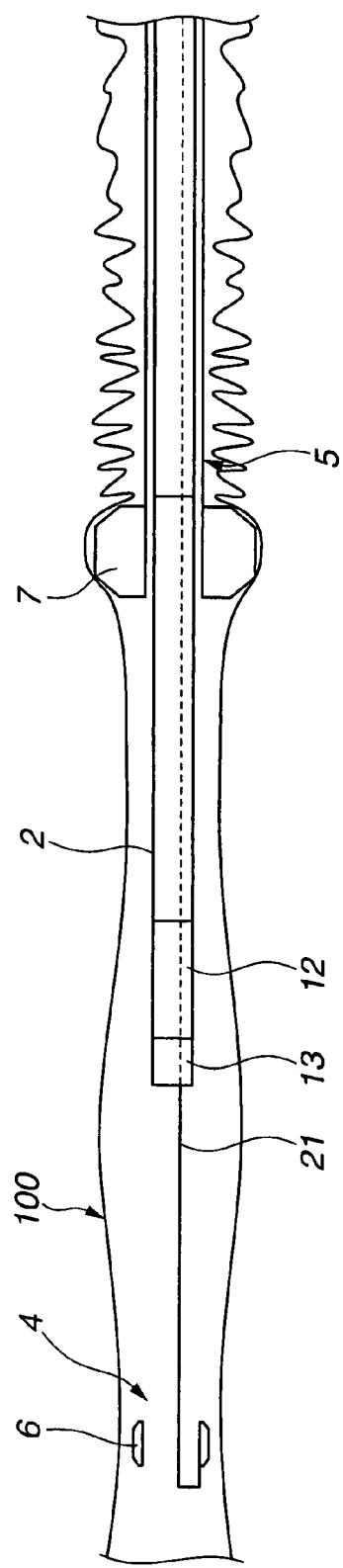
FIG. 12 is a view showing a state in which the first balloon is contracted from the state shown in FIG. 11 and the insertion unit and the first endoscope insertion assisting device 4 are respectively advanced to the deep part of the intestinal tract.
Figure 13:
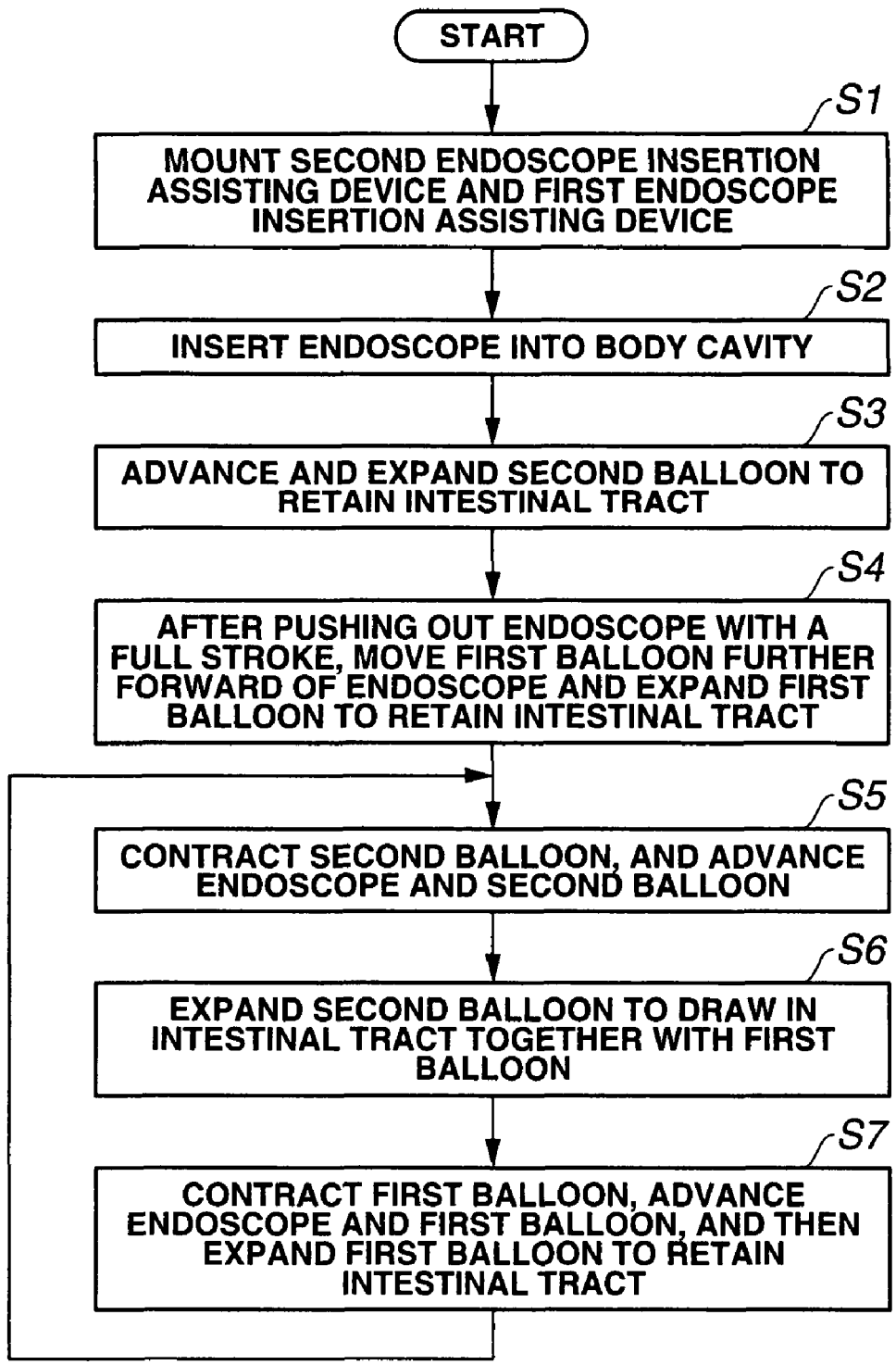
FIG. 13 is a flowchart for describing the operations according to the present embodiment which shows each of the states from FIG. 4 to FIG. 12 in a time series.

FIGS. 4 to 13 are views that describe operations according to the present embodiment. FIG. 4 is a view showing a state in which an endoscope is inserted and advanced using only the advance/retreat of the endoscope in a state in which a first and a second balloon are contracted. FIG. 5 is a view showing a state in which the second balloon is advanced toward the distal end of the endoscope from the state shown in FIG. 4. FIG. 6 is a view showing a state in which, after expanding the second balloon from the state shown in FIG. 5 to retain in the intestinal tract, the endoscope is pushed in with the maximum stroke. FIG. 7 is a view showing a state in which, in the state shown in FIG. 6, the shaft is pushed in to insert the first balloon into a deep part of the intestinal tract. FIG. 8 is a view showing a state in which, in the state shown in FIG. 7, the first balloon is expanded to retain the intestinal tract. FIG. 9 is a view showing a state in which, from the state shown in FIG. 8, a second balloon 7 is contracted and a second endoscope insertion assisting device and the insertion unit are then pushed forward to the deep part of the intestinal tract. FIG. 10 is a view showing a state in which, in the state shown in FIG. 9, the second balloon is expanded such that the intestinal tract is securely retained by the first and second balloons. FIG. 11 is a view showing a state in which, in the state shown in FIG. 10, an operation is performed to pull in the first and second endoscope insertion assisting devices and the insertion unit to draw in the intestinal tract. FIG. 12 is a view showing a state in which the first balloon is contracted from the state shown in FIG. 11, and the insertion unit and the first endoscope insertion assisting device 4 are respectively pushed forward to the deep part of the intestinal tract. FIG. 13 is a flowchart illustrating the operations according to the present embodiment.

Before conducting an examination using endoscopy, the technician inserts the insertion unit 3 of the endoscope 2 from the opening in the at-hand grip portion 33 of the tube element 32 of the second endoscope insertion assisting device 5, as shown in FIG. 1.

Next, the technician passes the shaft 21 of the first endoscope insertion assisting device 4 through the first channel opening 19 that is the distal side opening of the first channel 17, to mount the first endoscope insertion assisting device 4 in the vicinity of the outer peripheral surface of the distal end 13 of the endoscope 2 (in FIG. 1, the vicinity of the outer peripheral surface of the distal end 13 and the bending portion 12).

The rear end side of the shaft 21 is led to outside from the first channel insertion port 23, as shown in FIG. 1, such that the technician can grip the shaft 21 to perform an operation to advance or retreat the shaft 21.

When examining the inside of a body cavity, as shown in FIG. 4, the technician inserts the insertion unit 3 of the endoscope 2 into the body cavity from the distal side of the endoscope 2 in a state in which the first and second balloons 6 and 7 are respectively contracted. However, thereafter, when it becomes difficult for the distal end 13 of the endoscope 2 to advance further inside the body cavity, the present embodiment is operated according to the method as described below with reference to FIGS. 5 to 12.

First, as shown in FIG. 5, the technician grips the at-hand grip portion 33 of the second endoscope insertion assisting device 5 and pushes in the tube element 32 to move the second balloon 7 that is in a contracted state to the distal end 13 side of the endoscope 2.

Next, as shown in FIG. 6, the technician operates the second foot switch 31b to supply fluid to inside the second balloon 7 through the second fluid supply and exhaust line (not shown) by means of the balloon control device 8b, to thereby expand the second balloon 7 and retain the second endoscope insertion assisting device 5 in an intestinal tract 100.

Thereafter, as shown in FIG. 6, employing the second endoscope insertion assisting device 5 that is retained in the intestinal tract as an insertion guide, the technician pushes in the insertion unit 3 of the endoscope 2 with the maximum stroke with respect to the second endoscope insertion assisting device 5.

In this connection, the state on the side near the technician's hands at this time is one in which the at-hand grip portion 33 of the second endoscope insertion assisting device 5 is positioned fully at the end near the technician's hands of the insertion unit 3 of the endoscope 2.

Next, as shown in the FIG. 7, the technician pushes in the shaft 21 that extends outward from the first channel opening 19 of the operation unit 9, to thereby move the first balloon 6 to the side forward of the field of view from the top of the bending portion 12 and the distal end 13.

The reference symbol θ shown in FIG. 7 denotes the field of view range of the observation window 14. When the shaft 21 is pushed in and the first balloon 6 is moved to the side forward of the distal end 13 as shown in FIG. 7, the observation window 14 at the distal end 13 of the endoscope 2 is inside the field of view range θ, and an insertion operation can be performed while observing the operation.

At this time, the technician may freely adjust the rigidity of the shaft 21 by forming a loop of an arbitrary size and arbitrary number of windings at the rearward of the area around the technician's hands of the shaft 21 using the retaining member 30. More specifically, the insertion properties when pushing the first balloon 6 forward of the distal end 13 of the endoscope 2 can also be changed according to the preferences of the technician or to the site, enabling the insertion operation to be performed smoothly.

Next, as shown in FIG. 8, the technician operates the first foot switch 31*a* to supply fluid to inside the first balloon 6 through the first fluid supply and exhaust line 41 using the balloon control device 8*a*, to thereby expand the first balloon 6 and retain and immobilize the first balloon 6 inside the intestinal tract 100.

Thereafter, as shown in FIG. 9, the technician operates the second foot switch 31*b* to suck out the fluid from inside the second balloon 7 through the second fluid supply and exhaust line (not shown) using the balloon control device 8*b*, to contract the second balloon 7. Thereafter, the technician pushes forward the second endoscope insertion assisting device 5 and the distal end 13 of the endoscope 2 into the deep part of the intestinal tract 100, employing the shaft 21 of the first endoscope insertion assisting device 4 as an insertion guide. The state in which the second balloon 7 is contracted and the second endoscope insertion assisting device 5 and the distal end 13 of the endoscope 2 are again pushed forward to the first endoscope insertion assisting device 4 side is shown in FIG. 9.

In this case, according to the present embodiment, since the technician can view the first balloon 6 from the state shown in FIG. 8 to the state shown in FIG. 9 using the endoscope image, the technician can carefully push forward the insertion unit 3 of the endoscope 2 so that the intestinal tract 100 does not become wedged between the first balloon 6 and the distal end 13 of the endoscope 2.

Further, according to the present embodiment, in a case in which the intestinal tract 100 is folded up, for example, it is possible to push the endoscope 2 forward while carrying out a bending operation at the bending portion 12, and at the same time, moving the distal end 13 of the endoscope 2 toward the first balloon 6 in the field of view direction while sliding it on the shaft 21. Thereby, the distal end 13 of the endoscope 2 and the second endoscope insertion assisting device 5 can be surely moved to the first balloon 6 side. In this connection, since the first balloon 6 can be made into a large size, the retention force of the first balloon 6 can be increased such that the endoscope 2 can be advanced without fail.

Next, as shown in FIG. 10, the technician operates the second foot switch 31*b* to supply fluid to inside the second balloon 7 through the second fluid supply and exhaust line (not shown) by means of the balloon control device 8*b*, to thereby expand the second balloon 7 and retain the second endoscope insertion assisting device 5 in the intestinal tract 100. That is, as shown in FIG. 10, the first and second endoscope insertion assisting devices 4 and 5 can be retained without fail in the intestinal tract 100 by the first balloon 6 and the second balloon 7.

Thereafter, as shown in FIG. 11, in the state in which the first balloon 6 and the second balloon 7 are respectively expanded by fluid and are adjacent to each other, the technician performs an operation to slowly pull in the first and second endoscope insertion assisting devices 4 and 5 and the insertion unit 3 of the endoscope 2, to thereby draw in the intestinal tract 100 using the first and second balloons 6 and 7 that are expanded with fluid.

Next, as shown in FIG. 12, the technician operates the first foot switch 31*a* to suck out the fluid from inside the first balloon 6 through the first fluid supply and exhaust line 41 using the balloon control device 8*a*, to contract the first balloon 6. Thereafter, the technician pushes forward the first endoscope insertion assisting device 4 and the distal end 13 of the endoscope 2 into the deep part of the intestinal tract 100, employing the tube element 32 of the second endoscope insertion assisting device 5 as a guide, to thereby advance the endoscope 2. This state is the same as that shown in FIG. 7 as described above.

At this time, according to the present embodiment, since the intestinal tract 100 that is drawn is retained by the expanded second balloon 7 on the side nearer the technician, the intestinal tract 100 is not pushed back to its original position. Therefore, by repeating the above described operations, the technician can advance the distal end 13 of the endoscope 2 to a deep part of the intestinal tract 100 without fail and in a short time.

Further, according to the present embodiment, although not shown in the figures, the technician sometimes expands the first and second balloons 6 and 7 in a state in which the distal side of the endoscope 2 is inserted into a deep part side of the splenic curvature inside the large intestine to enter a state in which the first and second balloons 6 and 7 are immobilized inside the intestinal tract, and then performs an operation to slowly withdraw both the shaft 21 of the first endoscope insertion assisting device 4 and the tube element 32 of the second endoscope insertion assisting device 5 of the endoscope 2 at the same time to the side near the technician's hands. As a result, the technician can also straighten an intestine section such as the sigmoid colon section. Thus, by actively straightening the intestinal tract the technician not only facilitates the transmission of force to the tip of the endoscope 2, but can make the shaft 21 also function as an insertion guide of the endoscope 2. Consequently, the technician can advance the tip of the endoscope 2 to a deep part of the intestinal tract by not only drawing in the intestinal tract, but also by advancing the endoscope 2.

By combining drawing in of the intestinal tract and straightening of the intestinal tract, and repeating these operations several times, the endoscope 2 can ultimately be inserted into the deepest part of the intestinal tract.

FIG. 13 is a flowchart that shows an outline of the method of assisting insertion of the insertion unit 3 as illustrated in the above described FIGS. 4 to 12.

In the first step S1, the technician mounts the first endoscope insertion assisting device 4 and the second endoscope insertion assisting device 5 on the insertion unit 3 of the endoscope 2 as described above.

Next, as described in step S2, the technician inserts the insertion unit 3 of the endoscope 2 into a body cavity, for example, from the anus into the intestinal tract of the large intestine, from the distal end 13 side thereof.

When insertion is difficult when performing an operation to push in the insertion unit 3, as described in step S3, the technician pushes the second balloon 7 to the distal side of the endoscope 2 and expands the second balloon 7, and as shown in FIG. 6, retains and immobilizes the second balloon 7 inside the intestinal tract.

Subsequently, in step S4, as shown in FIG. 7, after pushing forward both the endoscope 2 and the first balloon 6 with a full stroke, the technician expands the first balloon 6 to retain and immobilize the first balloon 6 inside the intestinal tract (see FIG. 8).

Next, in step S5, as shown in FIG. 9, the technician contracts the second balloon 7 and pushes forward the second endoscope insertion assisting device 5 while employing the endoscope 2 as an insertion guide, and also pushes forward the endoscope 2 while employing the shaft 21 as an insertion guide.

In step S6, as shown in FIG. 10, the technician expands the second balloon 7 and performs a pulling operation to slowly pull the second balloon 7 and the first balloon 6 that is already expanded towards the side of the technician's hands, to thereby draw in the intestinal tract (see FIG. 11).

Next, in step S7, as shown in FIG. 12, the technician contracts the first balloon 6, and after pushing forward both the endoscope 2 and the first balloon 6 with a full stroke, expands the first balloon 6 to retain and immobilize the first balloon 6 inside the intestinal tract.

Thereafter, the operation returns to step S5 and the technician performs the series of operations to draw in the intestinal tract again and advance the endoscope 2 forward.

It is thus possible to smoothly insert the endoscope 2 into the deep part side of the intestinal tract.

Therefore, according to the present embodiment it is possible to individually move the first balloon 6 and the second balloon 7 with respect to the endoscope 2. Consequently, according to the endoscope apparatus 1 of the present embodiment, it is possible to increase the length of the maximum stroke (distance of maximum space between the first balloon 6 and the second balloon 7) for one advance/retreat (one time) that draws in the intestinal tract, without increasing the length of the insertion unit 3 of the endoscope 2. More specifically, since the stroke length when drawing in the intestinal tract one time can be increased even when the insertion unit 3 of the endoscope 2 has a length that is substantially the same as the conventional length, it is possible to insert the endoscope 2 into the deep part of the intestinal tract with good efficiency, and to shorten the examination time.

Further, since the technician can advance and retreat the endoscope 2 in a state in which the first balloon 6 and the second balloon 7 are both expanded and retain the intestinal tract, observation and treatment can be performed while stabilizing the inner wall of the intestinal tract between the first and second balloons 6 and 7 without affecting the peristaltic advance/retreat of the intestine.

Since the shaft 21 of the first endoscope insertion assisting device 4 has the same flexibility as an ordinary treatment instrument, and the curvature radius thereof is also small, there is an advantage that, it can allow the first balloon 6 to easily pass through even a curved section that has a small curvature radius inside a body cavity.

Further, since it is possible to visually check the first balloon 6 using the endoscope image, the technician can perform an operation to expand or contract the first balloon 6 with greater assurance. Since the tube element 32 of the second endoscope insertion assisting device 5 is transparent, by positioning the distal end 13 of the endoscope 2 further towards the side of the technician's hands than the second balloon 7, the technician can view the state of the intestinal wall along the full length of the insertion unit 3 beyond the transparent tube element 32 as well as the second balloon 7.

Furthermore, according to the endoscope apparatus 1 of the present embodiment, since the first balloon 6 can be moved outside the field of view by pulling the shaft 21 completely inside the insertion unit 3 of the endoscope 2, the first balloon 6 does not hinder observation or treatment. Also, since the shaft 21 comprises a flexible material as described above, even in a state in which the first balloon 6 is stored on the outside of the distal end 13 of the endoscope 2, an operation to bend the endoscope 2 can be performed without any hindrance.

Since the first balloon 6 is mounted on the balloon retaining member 37 that is at least thicker than the distal end 13, in comparison to, for example, the case of a balloon such as that of a balloon catheter that is used by passing the balloon through a first channel from the side of the technician's hands, a large size balloon for which the immobilizing force with respect to the intestinal tract is large can be used.

Further, since a bending operation of the endoscope 2 can be performed even in a state in which the first balloon 6 is pushed forward of the endoscope 2, the endoscope 2 can be inserted into a deeper part of the intestinal tract by subtly controlling the position of the first balloon 6 using a bending operation.

Furthermore, since the dimensions of the distal end of the second endoscope insertion assisting device 5 are designed so that it touches the end of the balloon retaining member 37, the first balloon 6 will not be damaged by the distal end of the second endoscope insertion assisting device 5.

By having the foregoing effects, according to the present embodiment it is possible to obtain the endoscope apparatus 1 that has superior operability.

The endoscope apparatus 1 according to the first embodiment may also be configured based on the first modification example shown in FIG. 14 or the second modification example shown in FIG. 15 as described later. The first modification example and the second modification example are described below.

Figure 14:
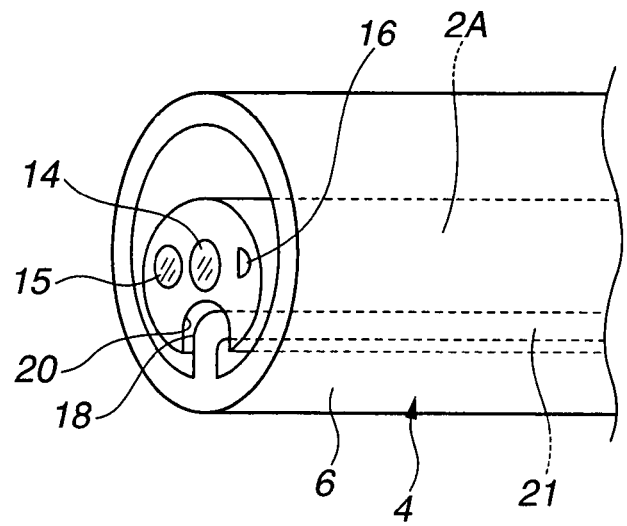
FIG. 14 is a magnified view of a distal end 13 of an endoscope 2 that is mounted with the first endoscope insertion assisting device according to a first modification example of the first embodiment.

FIG. 14 is a magnified view of the distal end 13 of an endoscope 2A that is mounted with the first endoscope insertion assisting device 4 according to the first modification example of the first embodiment. FIG. 15 is a magnified view of the distal end 13 of the endoscope 2A that is mounted with a first endoscope insertion assisting device 4A according to the second modification example of the first embodiment.

The endoscope apparatus 1 according to the first embodiment may use the endoscope 2A shown in FIG. 14 in place of the endoscope 2. As shown in FIG. 14, the endoscope 2A is configured with only the second channel 18, and does not have the first channel 17.

The insertion unit 3 of the endoscope 2A has a clearance between the shaft 21 and the second channel 18. Accordingly, a suction function in the endoscope 2 can be ensured by using the clearance provided between the shaft 21 and the second channel 18. Further, when using a treatment instrument also, the treatment instrument can be passed through the clearance to protrude from the second channel opening 20 into the body cavity.

Since the endoscope 2A does not require a dedicated channel (first channel) only for operating the first endoscope insertion assisting device 4, although suction performance and treatment performance are somewhat inferior to the endoscope 2 of the first embodiment, it can be used with a conventional single-channel endoscope and the range of adaptation can be broadened.

In the first modification example, the first endoscope insertion assisting device 4 and the second endoscope insertion assisting device 5 may be configured so as to constitute a common insertion assisting device with respect to the endoscope 2 for which the insertion unit 3 is thick and the endoscope 2A for which the insertion unit 3 is narrow, respectively.

Figure 15:
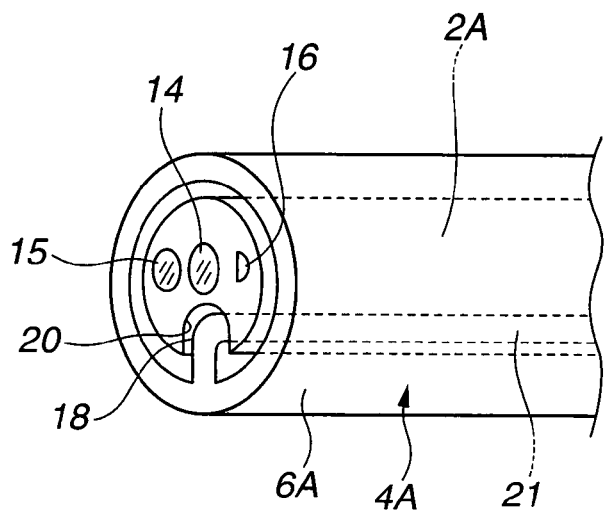
FIG. 15 is a magnified view of a distal end of the endoscope that is mounted with the first endoscope insertion assisting device according to a second modification example of the first embodiment.

Further, with respect to the first endoscope insertion assisting device 4 and the second endoscope insertion assisting device 5, as illustrated in the second modification example shown in FIG. 15, a plurality of kinds of endoscope insertion assisting devices that are suited to the thickness of the insertion unit 3 of each endoscope may be provided so that the first endoscope insertion assisting device 4A and the second endoscope insertion assisting device (not shown) on which are mounted balloons of sizes corresponding to the preference of the technician or to the observation site can be appropriately selected.

However, as shown in FIG. 14, when adopting a configuration in which endoscopes that are different to the thickness of the first endoscope insertion assisting device 4 are commonly used, it is necessary to make a shortest distance L (see FIG. 3) from the channel opening to the outer periphery of the distal end substantially the same for each endoscope.

In this connection, according to the second modification example, an operating method as described later may be carried out to insert the endoscope 2A into the body cavity. This operating method will be described using FIGS. 16 to 19.

FIGS. 16 to 19 are views for describing another operating method using the endoscope 2A according to the second modification example shown in FIG. 15 and first and second endoscope insertion assisting devices 4A and 5A.

According to this operating method, first, as shown in FIG. 16, the technician inserts the narrow single-channel endoscope 2A and the narrow first endoscope insertion assisting device 4A that are suited to the narrow single-channel endoscope 2A and narrow second endoscope insertion assisting device 5A into a deep part of the intestinal tract 100 in a combined state.

Thereafter, as shown in FIG. 17, the technician expands a first balloon 6A to retain and immobilize the inside of the intestinal tract 100, leaves the first endoscope insertion assisting device 4A in that state inside the intestinal tract 100, and withdraws the endoscope 2B and the second endoscope insertion assisting device 5A from the intestinal tract 100.

Figure 18:
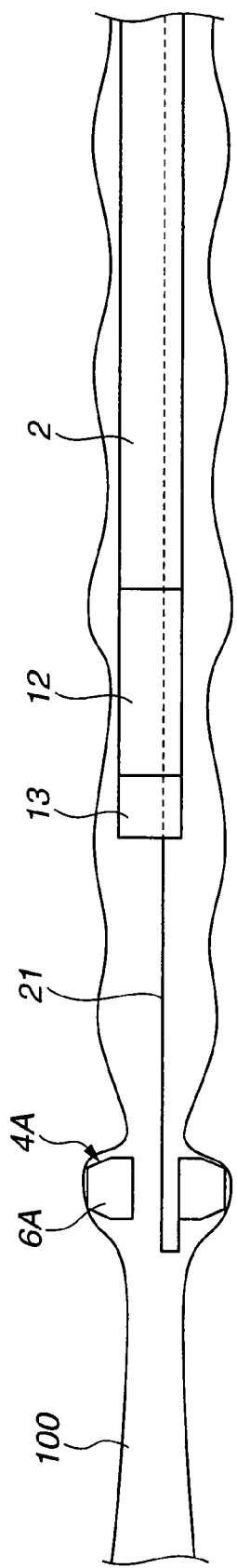
FIG. 18 is a view showing a state in which a two-channel endoscope is inserted in the state shown in FIG. 17.
Figure 19:
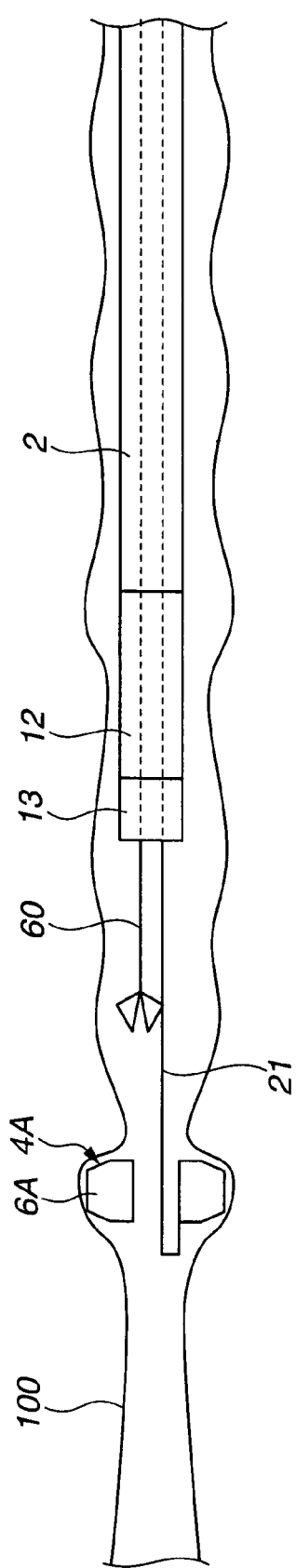
FIG. 19 is a view showing a state in which a treatment instrument is passed through a channel of the two-channel endoscope in the state shown in FIG. 18.

Next, as shown in FIG. 18, the technician inserts a two-channel endoscope 2 inside the intestinal tract 100 while sliding it along the shaft 21 that is passed through the first channel 17 as an insertion guide. Subsequently, as shown in FIG. 19, the technician passes a treatment instrument 60 through the second channel 18 to cause the treatment instrument 60 to protrude from the second channel opening 20 to treat or perform therapy for a deep part of the lumen of the intestinal tract 100.

More specifically, according to this operating method, the narrow endoscope 2A and the narrow first endoscope insertion assisting device 4A that are easy to insert are used to perform the initial insertion into the deep part of the intestinal tract 100, and thereafter, as required, a thick endoscope 2 that is exclusively for treatment, for example, the two-channel endoscope 2, is substituted for the narrow endoscope 2A. This operating method can also be applied to the second modification example.

The other configurations, actions and effects are substantially the same as in the first embodiment.

Figure 20:
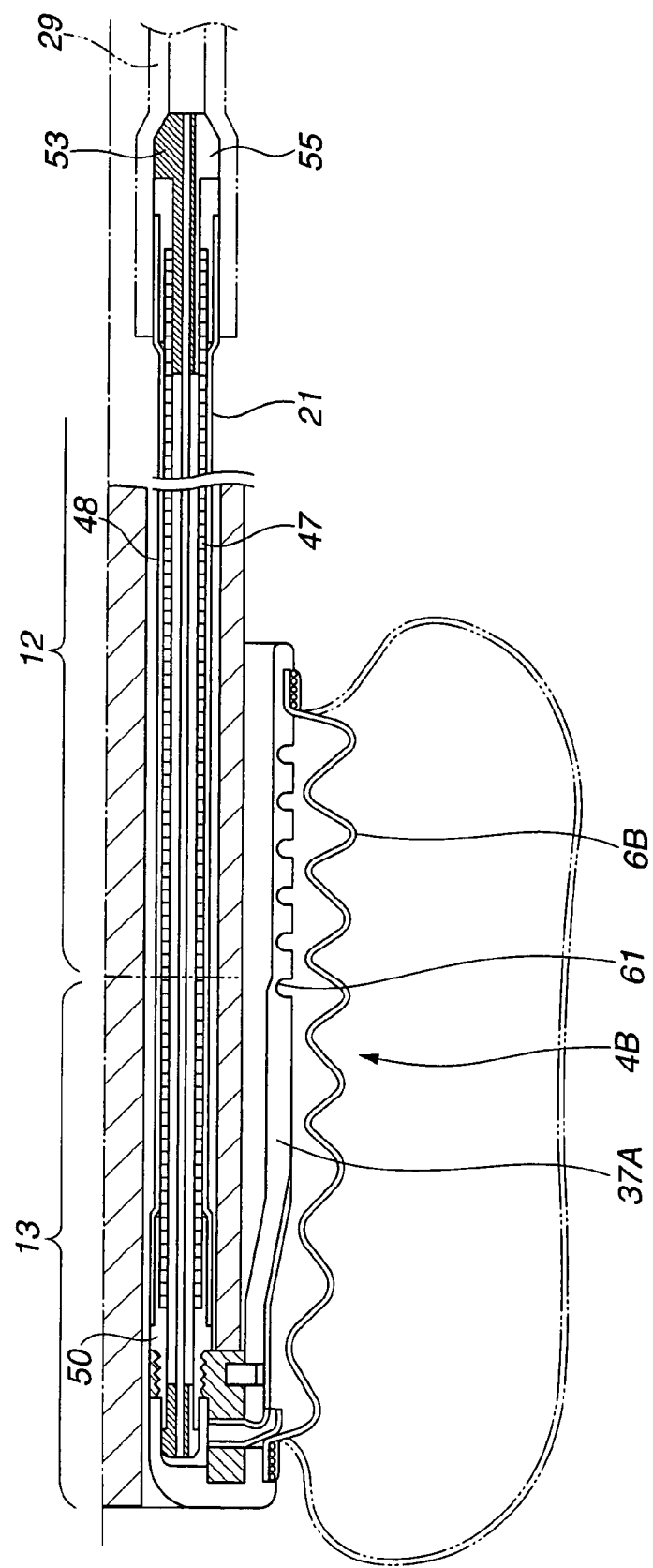
FIG. 20 is a sectional view in the longitudinal direction of the first endoscope insertion assisting device according to a third modification example of the first embodiment.

In the first embodiment, a configuration may also be adopted that uses a first endoscope insertion assisting device 4C as shown in the third modification example illustrated in FIG. 20. FIG. 20 shows a sectional view in the longitudinal direction of the first endoscope insertion assisting device according to the third modification example of the first embodiment.

As shown in FIG. 20, a first endoscope insertion assisting device 4B according to the third modification example has a balloon retaining member 37A that is formed longer in the insertion axis direction of the distal end 13 than the balloon retaining member 37 of the first endoscope insertion assisting device 4 according to the first embodiment. An additionally larger first balloon 6B is provided on the balloon retaining member 37A.

On the outer periphery of the balloon retaining member 37A on the side nearer the technician's hands, a plurality of concave portions 61 are formed at a section that corresponds to the bending portion 12 of the endoscope 2 when the shaft 21 is pushed in to the maximum. That is, by the formation of the plurality of concave portions 61, the balloon retaining member 37A has flexibility.

Thus, since the side near the technician's hands of the balloon retaining member 37A that is covered over the distal end 13 bends freely even when the bending portion 12 of the endoscope 2 is subjected to a bending operation, an operation to bend the bending portion 12 can be smoothly performed without any hindrance to the bending operation of the endoscope 2, and at the same time the insertability of the endoscope 2 can be enhanced utilizing the bending operation.

Further, according to the third modification example, since the first balloon 6B is provided, the retention force with respect to the intestinal tract can be increased in comparison to the first balloon 6 according to the first embodiment.

In this connection, in the third modification example, a structure having flexibility in the balloon retaining member 37A is not limited to the plurality of concave portions 61, and the balloon retaining member 37A may be configured using another structure as long as flexibility can be obtained.

The other configurations, actions and effects are substantially the same as in the first embodiment.

Second Embodiment

Next, the second embodiment of the present invention will be described with reference to FIG. 21.

Figure 21:
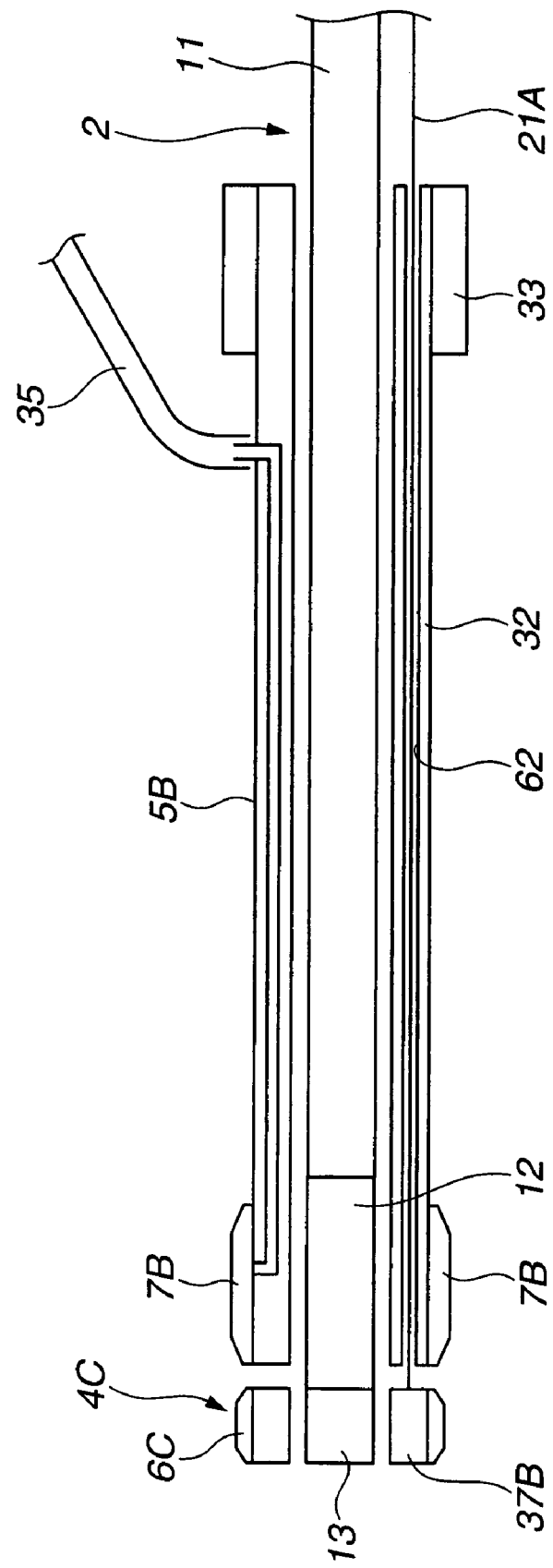
FIG. 21 is a sectional view in the longitudinal direction of the first and second endoscope insertion assisting device according to a second embodiment of the present invention.

FIG. 21 shows a sectional view in the longitudinal direction of a first and a second endoscope insertion assisting device according to the second embodiment of the present invention. In FIG. 21, components that are the same as components in the first embodiment are denoted by the same symbols and a description of those components is omitted hereunder, and only portions different to the first embodiment are described.

As shown in FIG. 21, a first endoscope insertion assisting device 4C and a second endoscope insertion assisting device 5B are provided on the endoscope apparatus 1 according to the present embodiment.

The first endoscope insertion assisting device 4C is configured so as to advance and retreat through a third channel 62 that is provided in the second endoscope insertion assisting device 5B.

A conventional narrow single-channel endoscope that is similar to the endoscope 2A shown in FIG. 16 is used for the endoscope 2 that is passed through the first and second endoscope insertion assisting devices 4C and 5B.

A shaft 21A of the first endoscope insertion assisting device 4C passes through the inside of the third channel 62 via a channel opening on the distal side to extend to the outside more than the at-hand grip portion 33.

According to the present embodiment, a configuration may be adopted in which the third channel 62 is formed within the wall thickness of the tube element 32, or is formed by adherently fixing a narrow tube to the outer surface or inner surface of the tube element 32.

The other configurations, actions and effects are substantially the same as in the first embodiment.

Third Embodiment

Next, the third embodiment of the present invention will be described with reference to FIGS. 22 to 36.

Figure 22:
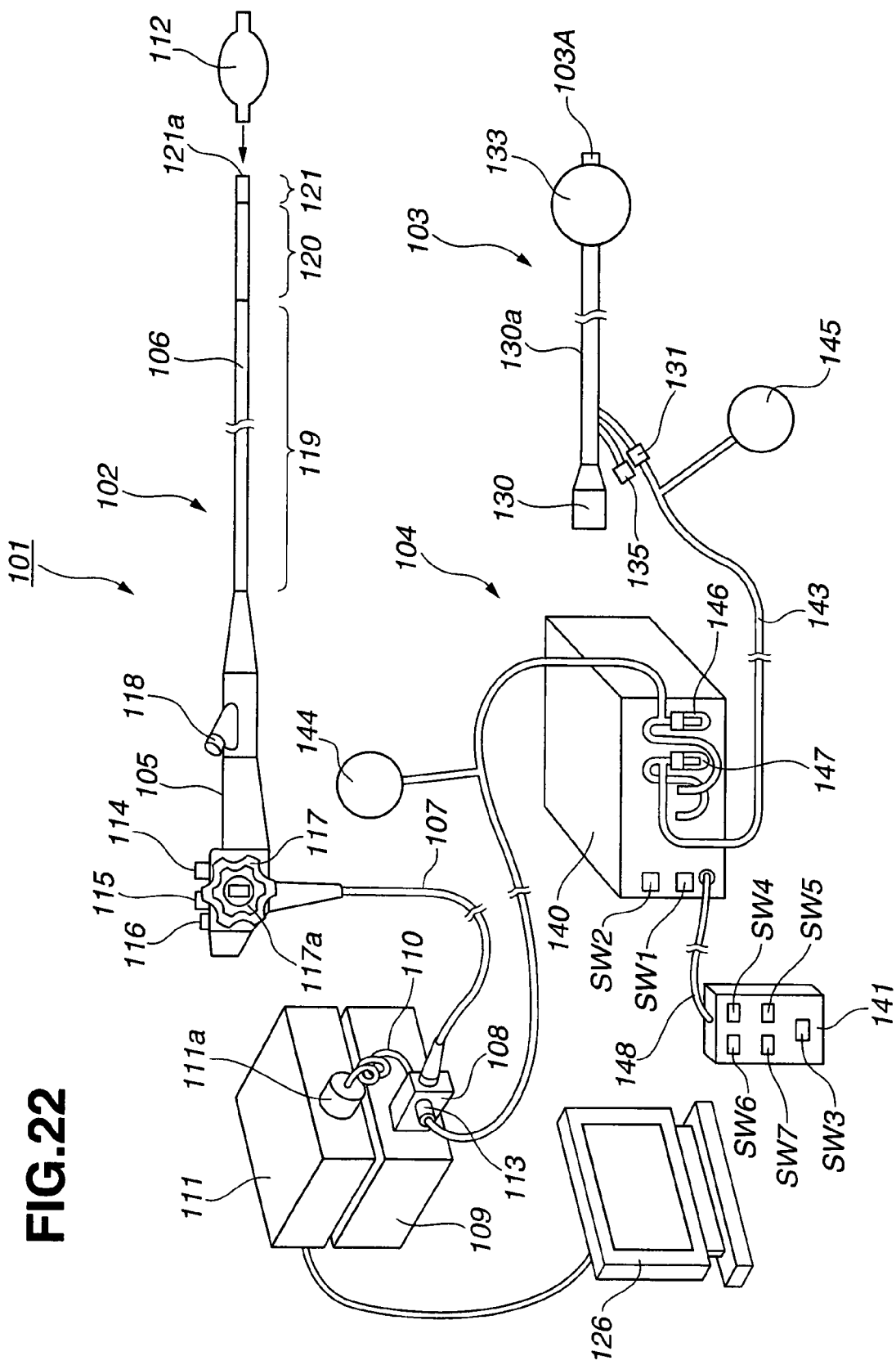
FIG. 22 is a system configuration diagram in a case in which a medical treatment device according to a third embodiment of the present invention is configured as an endoscope apparatus.
Figure 23:
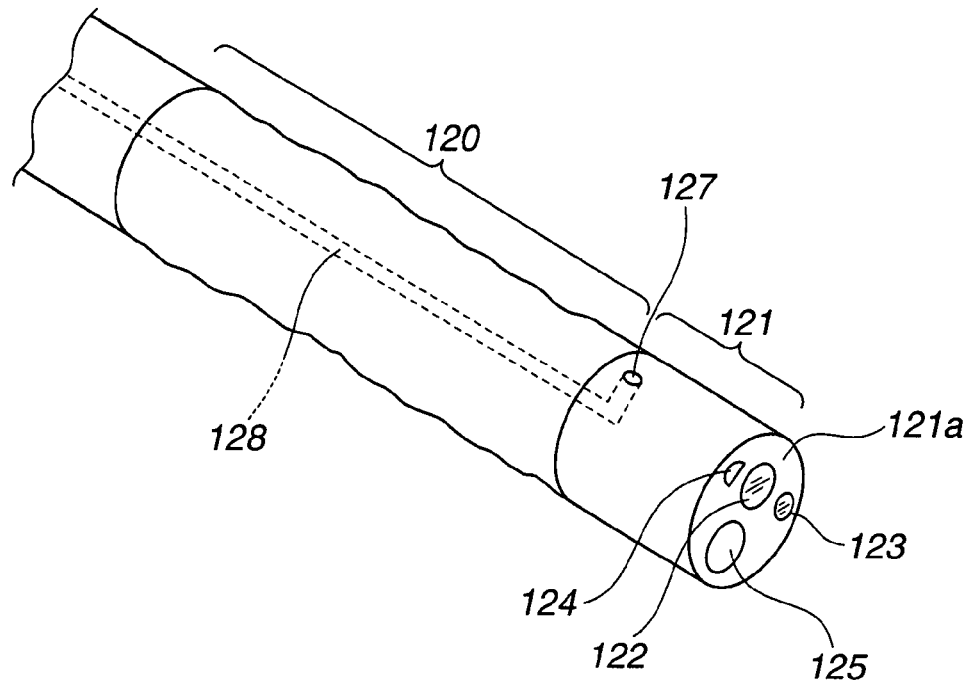
FIG. 23 is an oblique perspective view that shows the configuration of the distal end of the insertion unit of the endoscope.
Figure 24:
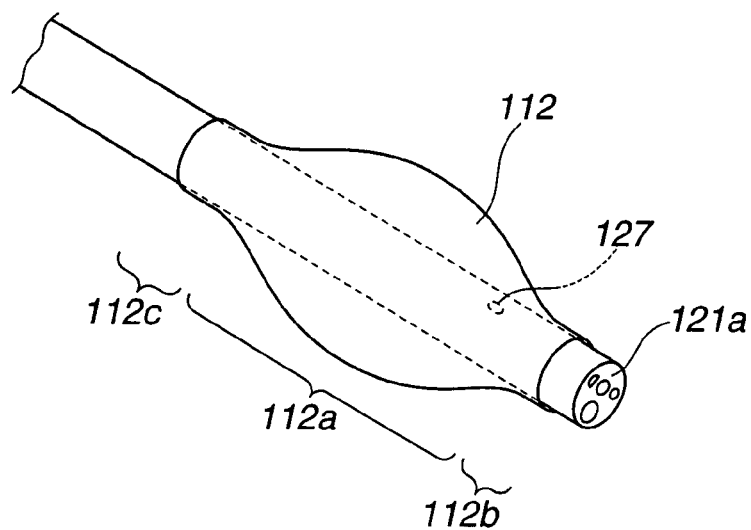
FIG. 24 is an oblique perspective view that shows the configuration of the distal end of the insertion unit that is provided with the first balloon.
Figure 25:
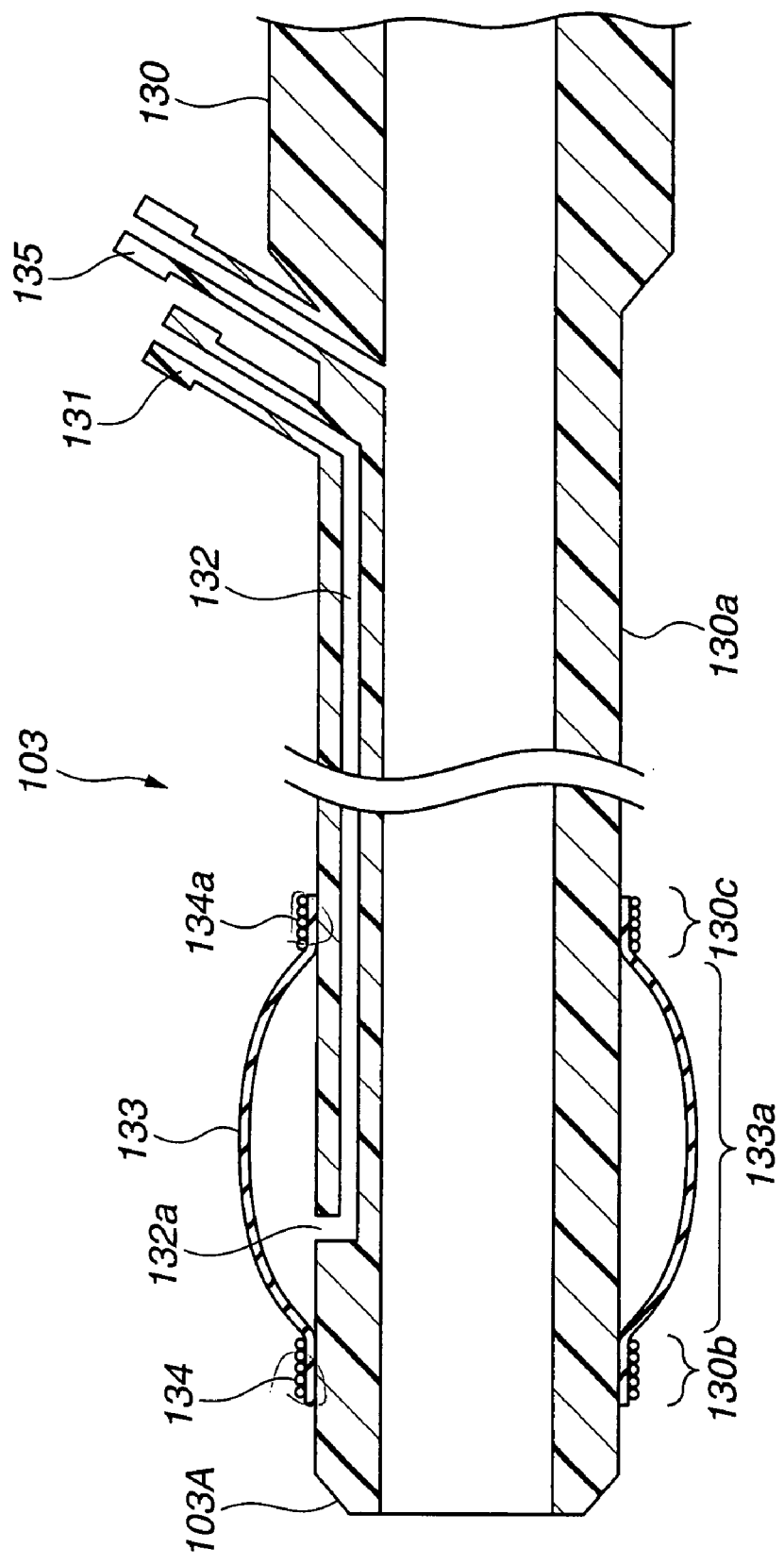
FIG. 25 is a sectional view showing the configuration of an overtube.
Figure 26:
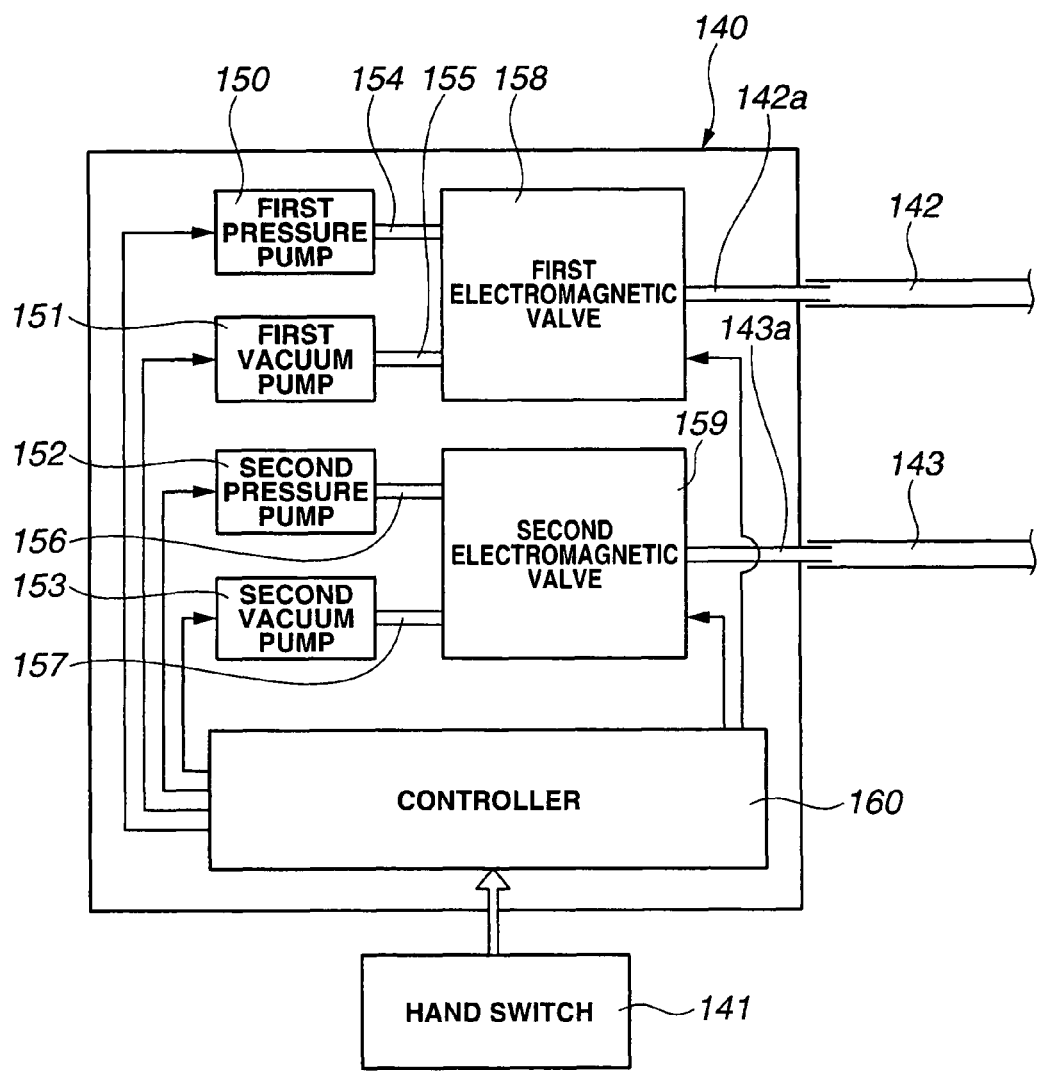
FIG. 26 is a block diagram showing the configuration of a balloon control device.
Figure 27:
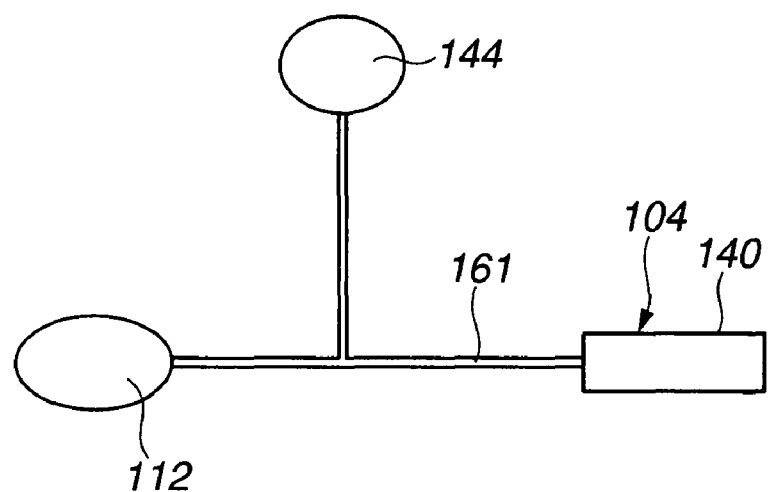
FIG. 27 is an explanatory drawing that shows a state in which air is supplied to the first and the second balloon through a supply line from the balloon control device.
Figure 28:
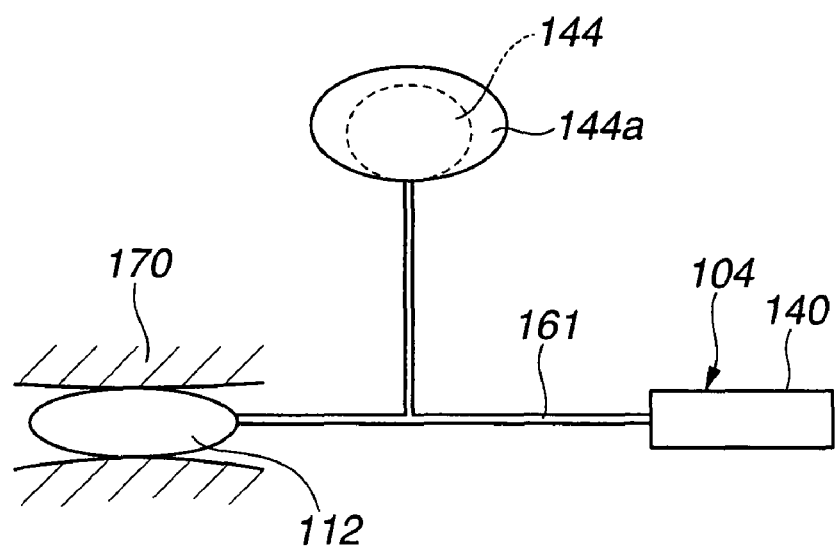

FIGS. 22 to 36 relate to a third embodiment of a medical treatment device according to the present invention. FIG. 22 is a system configuration diagram in a case in which the medical treatment device is configured as an endoscope apparatus. FIG. 23 is an oblique perspective view that shows the configuration of the distal end of an insertion unit of the endoscope. FIG. 24 is an oblique perspective view that shows the configuration of the distal end of the insertion unit when a first balloon is mounted thereon. FIG. 25 is a sectional view showing the configuration of an overtube. FIG. 26 is a block diagram showing the configuration of a balloon control device. FIGS. 27 and 28 are explanatory drawings for describing an action whereby a first balloon that is inserted inside a body cavity and a second balloon that is disposed outside the body cavity move in synchronization with each other. FIGS. 29 to 36 are explanatory drawings that illustrate a method of operating the endoscope apparatus.

As shown in FIG. 22, an endoscope apparatus 101 as the medical treatment device according to the present embodiment chiefly comprises an endoscope 102, an overtube 103 and a balloon control device 104. The endoscope apparatus 101 is also provided with a light source device 109, a signal processing device 111 such as a video processor, and a monitor 126 which are described later.

A first balloon 112 can be attached and detached to a distal end 121 of the endoscope 102, which is inserted into a body cavity (lumen) to be used for endoscopy. The overtube 103 allows an insertion unit 106 which is an insertion portion inserted into a body cavity and the like of the endoscope 102 of the present embodiment to pass therethrough, and has a third balloon 133. The balloon control device 104 controls the supply and exhaust of a fluid (refers to the supply or suction of a fluid) with respect to the first balloon 112 and the third balloon 133.

The endoscope 102 has an at-hand operation unit 105, a long and slender insertion unit 106 that connects in a row arrangement to the at-hand operation unit 105 and is inserted into a body cavity or the like, and a universal cable 107 that extends out from a side section of the at-hand operation unit 105.

An LG connector unit 108 is provided at an end of the universal cable 107. The LG connector unit 108 is connected to the light source device 109. The LG connector unit 108 is also connected to an electric connector 111a via a cable 110, and the electric connector 111a is connected to the signal processing device 111.

A first balloon air supply port 113 for supplying and exhausting fluid to and from the first balloon 112 is also provided in the LG connector unit 108. Although in the present embodiment, for example, air is used as the fluid, the fluid is not limited thereto and a different fluid may be used.

On the at-hand operation unit 105, an air supply and water supply button 114, a suction button 115, and a shutter button 116 are provided in proximity in a row arrangement, and a pair of angle knobs 117 and 117a and a forceps insertion port 118 are also provided thereon.

By operating the air supply and water supply button 114, the technician can perform the supply of air or the supply of water from an air supply and water supply nozzle 124 provided at the distal end 121. The technician can also operate the suction button 115 to suck body fluids or the like from a channel opening 125 at the distal end 121.

Further, by operating the shutter button 116 the technician can record an endoscope image corresponding to a site under observation in an unshown storage unit. The technician can also rotationally operate the angle knobs 117 and 117a with the fingers of the hand that grips the operation unit 105 to bend a bending portion 120, described later, in an arbitrary direction upward, downward, left or right by that rotational operation.

The insertion unit 106 comprises a flexible tube portion 119 that is long and slender and has flexibility, the bending portion 120 that is connected to the tip of the flexible tube portion 119 and which is bendable, and a rigid distal end 121 that is connected to the tip of the bending portion 120.

Although not shown in the figure, the bending portion 120 comprises a plurality of annular bending elements that are rotatably connected in the longitudinal direction of the bending portion 120, and the individual bending elements comprising the banding portion 120 can be rotated and bent by a rotational operation of the angle knobs 117 and 117a via a bending wire.

As shown in FIG. 23, on a distal end face 121a of the distal end 121, an objective lens (also referred to as "observation window") 122 comprising an objective optical system, an illumination lens 123, the air supply and water supply nozzle 124, and the channel opening 125 and the like are provided.

A light guide (not shown) that transmits an illumination light is passed through the inside of the illumination lens 123. The light guide (not shown) is passed through the inside of the insertion unit 106 and the like, and is detachably connected to the LG connector unit 108 of the light source device 109. An illumination light that is generated at the light source device 109 is transmitted by the light guide and radiated from the illumination lens 123 to thereby illuminate the inside of the body cavity as the field of view range of the objective lens 122.

At an image formation position at the rear of the objective lens 122, for example, a CCD (not shown) is disposed as an image pickup device. The CCD (not shown) performs photoelectric conversion of optical images of inside the body cavity that are formed on the image pickup surface.

Although not shown in the figure, the CCD is connected to a signal cable (not shown), and the signal cable passes through the insertion unit 106, the at-hand operation unit 105, the universal cable 107, and the cable 110 of FIG. 22 to extend as far as the electric connector 111a. Thereby, the CCD is electrically connected to the signal processing device 111. The signal processing device 111 performs signal processing for image pickup signals that were picked up by the CCD, to thereby generate video signals and output them to the monitor 126. As a result, optical images of inside the body cavity that are picked up by the CCD are displayed on the monitor 126.

As shown in FIG. 23 and FIG. 24, an air supply and suction port 127 is provided on the outer peripheral surface of the distal end 121. The air supply and suction port 127 is connected to the first balloon air supply port 113 shown in FIG. 22 via an air supply tube 128 having, for example, an inner diameter of around 0.8 mm that is passed through the inside of the insertion unit 106.

Accordingly, when air as a fluid is supplied to the first balloon air supply port 113, air spurts out from the air supply and suction port 127 of the distal end 121. Further, when air is sucked from the first balloon air supply port 113, air is sucked in from the air supply and suction port 127 of the distal end 121.

As shown in FIG. 24, the first balloon 112 that is formed using an elastic material such as rubber is detachably connected at the distal end 121 of the insertion unit 106. The first balloon 112 comprises a central expansion and contraction portion 112a, a distal side fitting portion 112b on the distal side of the expansion and contraction portion 112a, and a rear end side fitting portion 112c on the rear end side of the expansion and contraction portion 112a. The first balloon 112 is attached so that the air supply and suction port 127 is disposed on the inner side of the expansion and contraction portion 112a. Unshown threads are wound around the distal side fitting portion 112b and the rear end side fitting portion 112c such that distal side fitting portion 112b and the rear end side fitting portion 112c are fixed to adhere around the circumference of the outer peripheral surface of the insertion unit 106.

According to the present embodiment, instead of winding threads, the distal side fitting portion 112b and the rear end side fitting portion 112c may be fixed by fitting a fixing ring thereon.

A configuration may also be adopted in which, without using a fixing member such as a thread or a fixing ring, by previously forming the inner diameter between the distal side fitting portion 112b and the rear end side fitting portion 112c such that it is narrower than the outer diameter on the endoscope side, and widening the two fitting portions 112b and 112c so as to sheathe the distal end 121 when mounting, the fitting portions 112b and 112c are adhered and fixed by only the elastic fastening force of the two fitting portions 112b and 112c in the state in which mounting is completed.

In the first balloon 112 that is mounted in this manner, the expansion and contraction portion 112a is expanded in a substantially spherical shape by blowing air out from the air supply and suction port 127, and by sucking air from the air supply and suction port 127 the expansion and contraction portion 112a is contracted to stretch over the outer peripheral surface of the distal end 121.

As shown in FIG. 22 and FIG. 25, the overtube 103 is formed in a cylindrical shape and has an inner diameter that is slightly larger than the outer diameter of the insertion unit 106, and also has abundant flexibility. A rigid grip portion 130 is provided at the proximal portion of the overtube 103, and the insertion unit 106 is inserted from an opening on the grip portion 130 side.

As shown in FIG. 25, a balloon air supply port 131 is provided in the vicinity of the grip portion 130 of the overtube 103. An air supply tube 132 having an inner diameter of, for example, 1 mm is connected to the balloon air supply port 131. The air supply tube 132 is formed so as to be disposed inside the wall thickness (more specifically, around 1 mm to 3 mm inside the wall thickness) of the overtube 103, and extends as far as the distal end of the overtube 103.

A taper is formed at a distal end 103A of the overtube 103 to form a tapered shape. Further, a third balloon 133 that is formed from an elastic member such as rubber is mounted adjacent to the distal end 103A of the overtube 103. The third balloon 133 is mounted in a state in which the overtube 103 passes therethrough, and has a central expansion and contraction portion 133a, a distal side fitting portion 130b and a rear end side fitting portion 130c.

Threads 134 and 134a are wound around the distal side fitting portion 130b and the rear end side fitting portion 130c to fix the two fitting portions to the overtube 103.

The expansion and contraction portion 133a is formed in a substantially spherical shape in a natural state (i.e. a state in which it is neither expanded nor contracted). The third balloon 133 is configured such that the size of the substantially spherical shape satisfies any one of the following relations: the size is larger than the size of the first balloon 112 in a natural state, smaller than the size of the first balloon 112 in a natural state, or substantially the same size as the first balloon 112 in a natural state.

The third balloon 133 is also configured such that when air of the same pressure is supplied to the first balloon 112 and the third balloon 133, respectively, the outer diameter at the time of expansion of the expansion and contraction portion 130a of the third balloon 133 satisfies any one of the relations: the outer diameter is larger than the outer diameter at the time of expansion of the expansion and contraction portion 112a of the first balloon 112, smaller than the outer diameter at the time of expansion of the expansion and contraction portion 112a, or substantially the same size as the outer diameter at the time of expansion of the expansion and contraction portion 112a.

The air supply tube 132 opens inside the expansion and contraction portion 133a to form an air supply and suction port 132a. Accordingly, when air is supplied from the third balloon air supply port 131, air blows out from the air supply and suction port 132a and the expansion and contraction portion 133a expands.

Further, when air is sucked from the third balloon air supply port 131, air is sucked from the air supply and suction port 132a and the third balloon 133 contracts. An inlet 135 for pouring a lubricant such as water inside the overtube 103 is provided adjacent to the grip portion 130 of the overtube 103.

As shown in FIG. 22, the balloon control device 104 is a device that supplies or sucks a fluid such as air to or from the first balloon 112 and also supplies or sucks a fluid such as air to or from the third balloon 133. The balloon control device 104 comprises a device main unit 140 and a hand switch for remote control 141. In this connection, the balloon control device 104 constitutes fluid supply means as a fluid supply portion.

On the front panel of the device main unit 140 are provided a power switch SW1 and a stop switch SW2. A first tube 142 for supplying air to or sucking air from the first balloon 112 and a second tube 143 for supplying air to or sucking air from the third balloon 133 are also attached to the front panel of the device main unit 140.

According to the present embodiment, partway along the first tube 142, a second balloon 144 for recognizing the supply or exhaust state of fluid with respect to the first balloon 112 is provided in a condition in which it links to the first tube 142. Further, partway along the second tube 143, a fourth balloon 145 for recognizing the supply or exhaust state of fluid with respect to the third balloon 133 is provided in a condition in which it links to the second tube 143.

In this connection, the first and third balloons 112 and 133 comprise balloons, and the second and fourth balloons 144 and 145 comprise elastic members.

Partway along the first tube 142 and the second tube 143 are provided a first fluid storage tank 146 and a second fluid storage tank 147 for preventing a backflow of body fluid when the first balloon 112 or the third balloon 133 burst.

The hand switch 141 has a stop switch SW3 that is similar to the stop switch SW2 on the device main unit 140 side, an ON/OFF switch SW4 for designating pressurization/decompression of the first balloon 112, a pause switch SW5 for retaining the pressure of the first balloon 112, an ON/OFF switch SW6 for designating pressurization/decompression of the third balloon 133, and a pause switch SW7 for retaining the pressure of the third balloon 133.

The hand switch 141 is electrically connected to the device main unit 140 through a cord 148, and outputs operation signals that correspond to various switch operations to the device main unit 140. The device main unit 140 performs control to perform operations based on the supplied operation signals.

The specific configuration of the device main unit 140 will now be described with reference to FIG. 26.

As shown in FIG. 26, inside the device main unit 140 are provided a first pressure pump 150, a first vacuum pump 151, and a first electromagnetic valve 158 that comprise the control system of the first balloon 112; a second pressure pump 152, a second vacuum pump 153, and a second electromagnetic valve 159 that comprise the control system of the third balloon 133; and a controller 160 that controls these pumps and valves.

The first pressure pump 150 and the first vacuum pump 151 are respectively connected to the first electromagnetic valve 158 through a pressure tube 154 and a vacuum tube 155. The first electromagnetic valve 158 is connected to the first tube 142 through a pressure and suction tube 142a, and the first tube 142 communicates with the first balloon 112.

Accordingly, the device main unit 140 is configured such that it is possible to communicate either the first pressure pump 150 or the first vacuum pump 151 with the first balloon 112 by controlling opening and closing operations of the first electromagnetic valve 158.

Similarly to the above, the second pressure pump 152 and the second vacuum pump 153 are respectively connected to the second electromagnetic valve 159 through a pressure tube 156 and a vacuum tube 157. The second electromagnetic valve 159 is connected to the second tube 143 through a pressure and suction tube 143a, and the second tube 143 communicates with the third balloon 133.

Accordingly, the device main unit 140 is configured such that it is possible to communicate either the second pressure pump 152 or the second vacuum pump 153 with the third balloon 133 by controlling opening and closing operations of the second electromagnetic valve 159.

The controller 160 controls the first and second pressure pumps 150 and 152, the first and second vacuum pumps 151 and 153, and the first and second electromagnetic valves 158 and 159 based on operation signals that are supplied from the hand switch 141.

More specifically, the controller 160 controls the first electromagnetic valve 158 based on an operation signal to cause either the first pressure pump 150 or the first vacuum pump 151 to communicate with the first balloon 112, and also to drive the first pressure pump 150 or the first vacuum pump 151 that is caused to communicate with the first balloon 112.

Further, the controller 160 controls the second electromagnetic valve 159 based on an operation signal to cause either the second pressure pump 152 or the second vacuum pump 153 to communicate with the third balloon 133, and also to drive the second pressure pump 152 or the second vacuum pump 153.

Thus, by operating the switch SW4 or switch SW6 of the hand switch, the technician can expand the first balloon 112 and/or the third balloon 133 by supplying air thereto or can contract the first balloon 112 and/or the third balloon 133 by sucking air therefrom by means of control by the controller 160.

Further, by controlling the first and second electromagnetic valves 158 and 159, both the first and second pressure pumps 150 and 152 and the first and second vacuum pumps 151 and 153 can be blocked off from the first balloon 112 and the third balloon 133. It is therefore possible to maintain the first balloon 112 and the third balloon 133 in an expanded state or a contracted state.

Next, the synchronized action of the first balloon 112 and the second balloon 144 that are a feature of the present embodiment will be described while referring to FIG. 27 and FIG. 28.

FIG. 27 is an explanatory drawing that shows a state in which air is supplied to the first and second balloons 112 and 144 through a supply line 161 from the balloon control device 104. FIG. 28 is an explanatory drawing that shows a state in which air is supplied to the supply line 161 from the balloon control device 104 in a state in which an expansion action of the first balloon 112 is restricted from outside by a body wall or the like.

In this connection, the supply line 161 corresponds to the air supply tube 128 and the first tube 142, or the air supply tube 132 and the second tube 143.

As shown in FIG. 27, when air is supplied to the first and second balloons 112 and 144, the first balloon 112 is expanded by the supply of air. At the same time, since the second balloon 144 communicates to the same supply line 161, because air of substantially the same pressure as that supplied to the first balloon 112 is supplied thereto, the second balloon 144 expands in synchrony with the expansion action of the first balloon 112.

In this case, for example, as shown in FIG. 28, if it is assumed that the expansion action of the first balloon 112 is restricted from outside by a body cavity wall 170 or the like, since the expansion action of the first balloon 112 in this state is restricted, air can not be supplied due to the internal pressure of the first balloon 112. Accordingly, air is supplied to the second balloon 144 side which is in a state in which the internal pressure is lower than the internal pressure of the first balloon 112, and as a result only the second balloon 144 further expands.

More specifically, according to the present embodiment a configuration is adopted such that, when the first balloon 112 is restricted in some manner inside a body cavity, the second balloon 144 that is provided outside the body cavity expands by that amount to let that pressure escape.

The aforementioned action is not limited to a state in which air is supplied continuously from the balloon control device 104, and the action is the same in the case of a closed line state in which air is not supplied.

More specifically, in a closed line state in which air was supplied once to expand the first balloon 112 and the supply of air was then stopped, when the shape of the first balloon 112 receives a restricting influence from outside and contracts, air corresponding to the amount that receives the restricting influence and contracts flows to the second balloon 144 that is disposed outside the body cavity. Therefore, since the second balloon 144 expands by the amount of air that flows thereto, the first balloon 112 acts to cause the pressure that is generated by the restriction to flow out.

In this connection, according to the present embodiment a configuration may be adopted in which the raw material or wall thickness of the like of the balloons are changed so that a pressure that starts expansion from the natural state of a balloon (i.e. a state in which the balloon is neither expanded or contracted) is higher for the second balloon 144 than for the first balloon 112. For example, by mounting a second balloon 144 for which the expansion starting pressure is 10 kpa, the fact that the second balloon 144 starts expanding generally indicates that the pressure inside the communicating supply line 161 and the pressure inside the first balloon 112 is a high pressure of 10 kpa or more. Therefore, it is easier for the user to recognize an abnormal pressure state with respect to the first balloon 112 in a body cavity.

Further, according to the present embodiment a configuration may also be adopted in which it is easy to recognize that the second balloon 144 is expanding from a natural state by employing a method whereby, when the second balloon 144 starts to expand from a natural state, the color of the second balloon 144 changes or characters or symbols appear on the peripheral surface of the second balloon 144. The present embodiment is not limited to these methods, and a configuration that uses another means may also be used as long as a user can easily distinguish between a natural state and an expansion state of the second balloon 144.

In this connection, since the configuration and characteristics of the third balloon 133 of the overtube 103 and the fourth balloon 145 are the same as the configuration and characteristics of the first balloon 112 and the second balloon 144, a description thereof is omitted here.

Next, the method of operating the endoscope apparatus configured as described above will be described referring to FIGS. 29 to 36.

Figure 29:
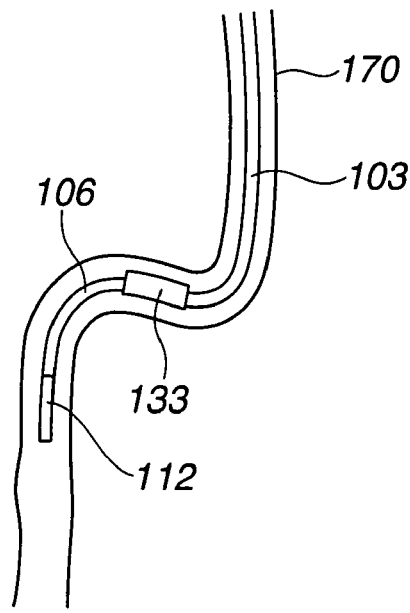
FIG. 29 is a view showing a state in which the insertion unit is inserted into an intestinal tract in a state in which the insertion unit is sheathed with the overtube.

First, as shown in FIG. 29, in a state in which the insertion unit 106 is covered with the overtube 103, the technician inserts the insertion unit 106 into an intestinal tract (for example, the descending part of duodenum) 170. At this time, the first balloon 112 and the third balloon 133 are contracted.

Figure 30:
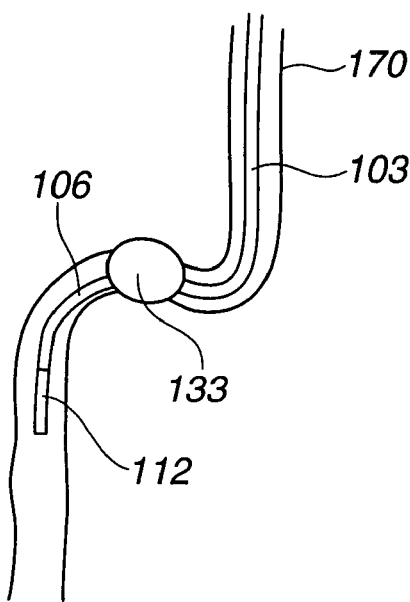
FIG. 30 is a view showing a state in which, in the state shown in FIG. 29, a third balloon is expanded to immobilize the overtube in the intestinal tract.

Next, as shown in FIG. 30, in a state in which the distal end 103A of the overtube 103 is inserted as far as a curved section of the intestinal tract (body cavity wall) 170, the technician supplies air to the third balloon 133 to expand the balloon 133.

As a result, the third balloon 133 is retained by the intestinal tract (body cavity wall) 170, and the distal end 103A of the overtube 103 is immobilized in the intestinal tract (body cavity wall) 170.

Figure 31:
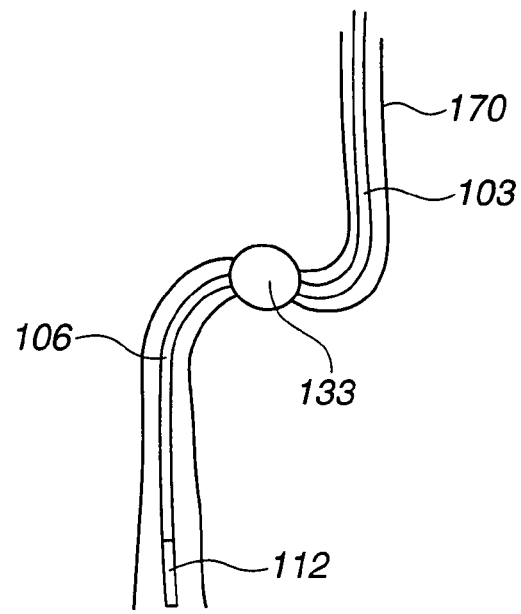
FIG. 31 is a view showing a state in which, from the state shown in FIG. 30, only the insertion unit of the endoscope is inserted into a deep part of the intestinal tract.
Figure 32:
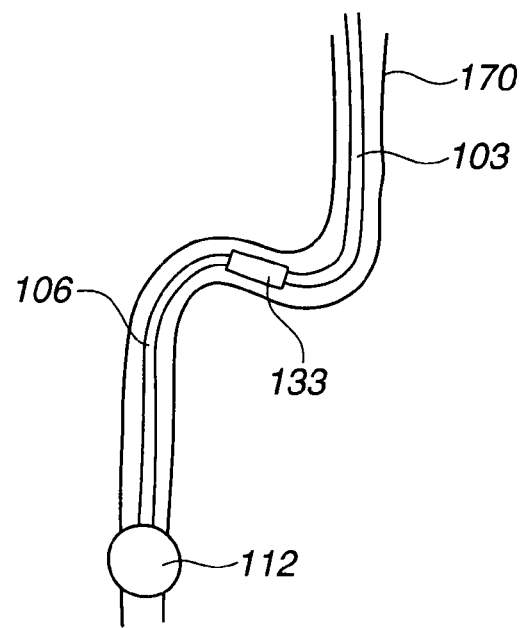
FIG. 32 is a view showing a state in which, in the state shown in FIG. 31, the first balloon is expanded such that it is immobilized in the intestinal tract.

Thereafter, as shown in FIG. 31, the technician performs an insertion operation to insert only the insertion unit 106 of the endoscope 102 into a deep part of the intestinal tract (body cavity wall) 170 (insertion operation). Subsequently, as shown in FIG. 32, the technician supplies air to the first balloon 112 to expand the first balloon 112. Thereby, the first balloon 112 is immobilized in the intestinal tract (body cavity wall) 170 (immobilizing operation).

Figure 33:
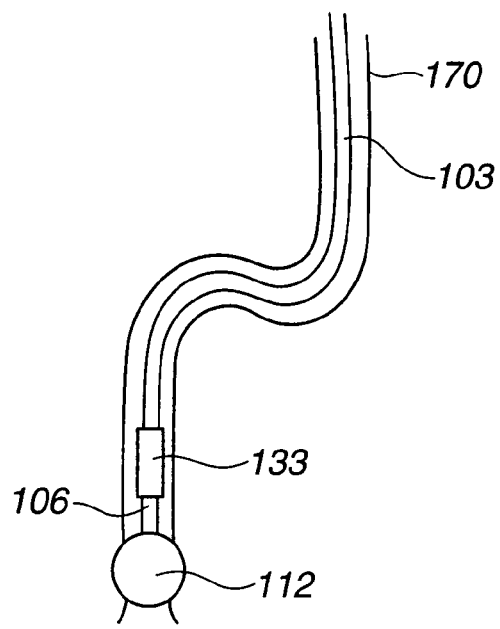
FIG. 33 is a view showing a state in which, in the state shown in FIG. 32, a pushing operation is performed to push in the overtube so that it is inserted along the insertion unit.

Next, after sucking air from the third balloon 133 to contract the third balloon 133, as shown in FIG. 33, the technician performs a pushing-in operation to push in the overtube 103 to insert it along the insertion unit 106 (pushing-in operation).

Figure 34:
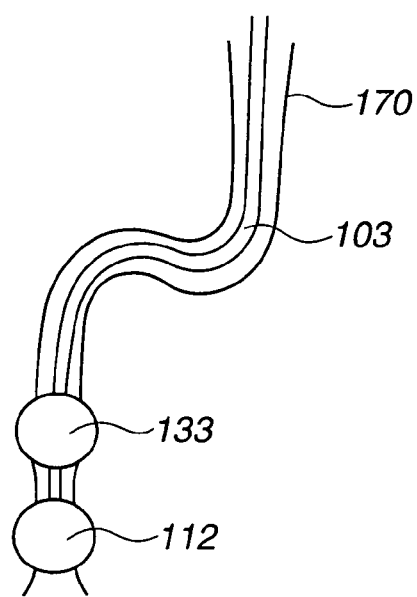
FIG. 34 is a view showing a state in which, in the state shown in FIG. 33, the third balloon is expanded to immobilize the third balloon in the intestinal tract.

Subsequently, after bringing the distal end 103A of the overtube 103 to a position adjacent to the first balloon 112, as shown in FIG. 34, the technician supplies air to the third balloon 133 to expand the third balloon 133. As a result, the third balloon 133 is immobilized in the intestinal tract (body cavity wall) 170. That is, the intestinal tract (body cavity wall) 170 is held by the third balloon 133 (holding operation).

Figure 35:
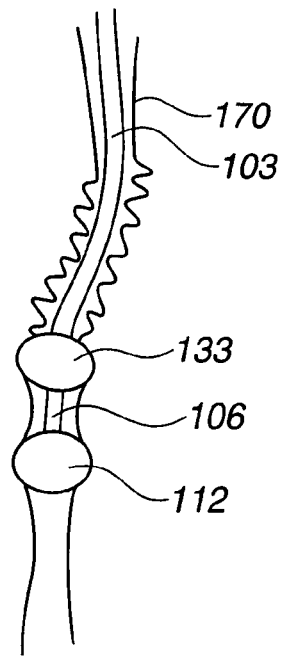
FIG. 35 is a view showing a state in which, in the state shown in FIG. 34, a drawing-in operation is performed to draw in the overtube.

Next, in this state, as shown in FIG. 35, the technician performs a drawing-in operation to draw in the overtube 103. As a result, the intestinal tract (body cavity wall) 170 enters a contracted state, and superfluous deformation or curving of the overtube 103 is eliminated.

Figure 36:
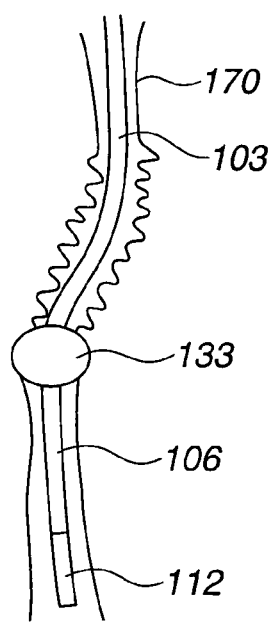
FIG. 36 is a view showing a state in which, in the state shown in FIG. 35, the first balloon is contracted and the distal end of the insertion unit is inserted as far as possible into a deep part of the intestinal tract.

Next, as shown in FIG. 36, the technician performs an operation to suck air from the first balloon 112 to contract the first balloon 112. The technician then inserts the distal end 121 of the insertion unit 106 as far as possible into the deep part of the intestinal tract (body cavity wall) 170. That is, the technician performs the insertion operation illustrated in FIG. 31 again. It is thereby possible to insert the distal end 121 of the insertion unit 106 into the deep part of the intestinal tract (body cavity wall) 170.

When inserting the insertion unit 106 further into the deep part, after performing an immobilizing operation as shown in FIG. 32, the technician performs a pushing-in operation as shown in FIG. 33, and then repeats the holding operation as shown in FIG. 34, the drawing in operation shown in FIG. 35, and the insertion operation shown in FIG. 36 in that order. It is thereby possible to insert insertion unit 106 further into the deep part of the intestinal tract (body cavity wall) 170.

When performing the above described operations, according to the present embodiment, since the second balloon 144 and the fourth balloon 145 are provided, by viewing the state of the second balloon 144 and the fourth balloon 145 the technician can be aware of the supply and exhaust state of fluid with respect to the first balloon 112 and the third balloon 133 that are inserted in the body cavity.

Consequently, according to the third embodiment, by providing the second and fourth balloons 144 and 145 for recognizing the supply and exhaust state of fluid with respect to the first balloon 112 and the third balloon 133 as described above, the supply and exhaust state of fluid with respect to the first balloon 112 and the third balloon 133 inside a body cavity can be recognized employing a simple configuration that does not require measuring means as a measuring portion for knowing the expansion condition (fluid supply and exhaust state) of a balloon in a body cavity of the balloon control device 104, and display means as a display unit that displays the expansion condition (fluid supply and exhaust state) of a balloon based on a measuring result obtained by the measuring means on the monitor 126. Hence, the balloon control device 104 can be made at a low cost.

Furthermore, in a case in which the expanded first balloon 112 is restricted from outside by a body wall or the like, because the second balloon 144 expands by that amount, a function as a safety device whereby the excessive pressure within the first balloon 112 is simply and quickly released can also be obtained.

Further, since the air that was released into the second balloon 144 is returned to inside the first balloon 112 by the restoring force of the second balloon 144 when the restricted state of the first balloon 112 is released, it is not necessary to perform additional air supply from the balloon control device 104, enabling the examination to be performed simply and quickly.

Accordingly, the state (condition) of the first balloon 112 can be ascertained from the state (condition) of the second balloon 144 that is on the side of the technician's hands. Further, the state (condition) of the third balloon 133 can be simply ascertained from the state (condition) of the fourth balloon 145 that is on the side of the technician's hands. Consequently, it is possible to prevent an operating mistake such as performing an operation to insert the insertion unit 106 and the overtube 103 into a body cavity in a state in which the first balloon 112 and the third balloon 133 are expanded, or an operation to draw in the insertion unit 106 and the overtube 103 in a state in which the first balloon 112 and the third balloon 133 are contracted.

In the present embodiment, the endoscope 102 need not use a double balloon system which is combined with a special endoscope provided with the first balloon 112 as shown in FIG. 22, and may use a single balloon system in which the balloon-attached overtube 103 shown in FIG. 22 is combined with a conventional endoscope that does not have a balloon attached thereto.

Fourth Embodiment

Figure 37:
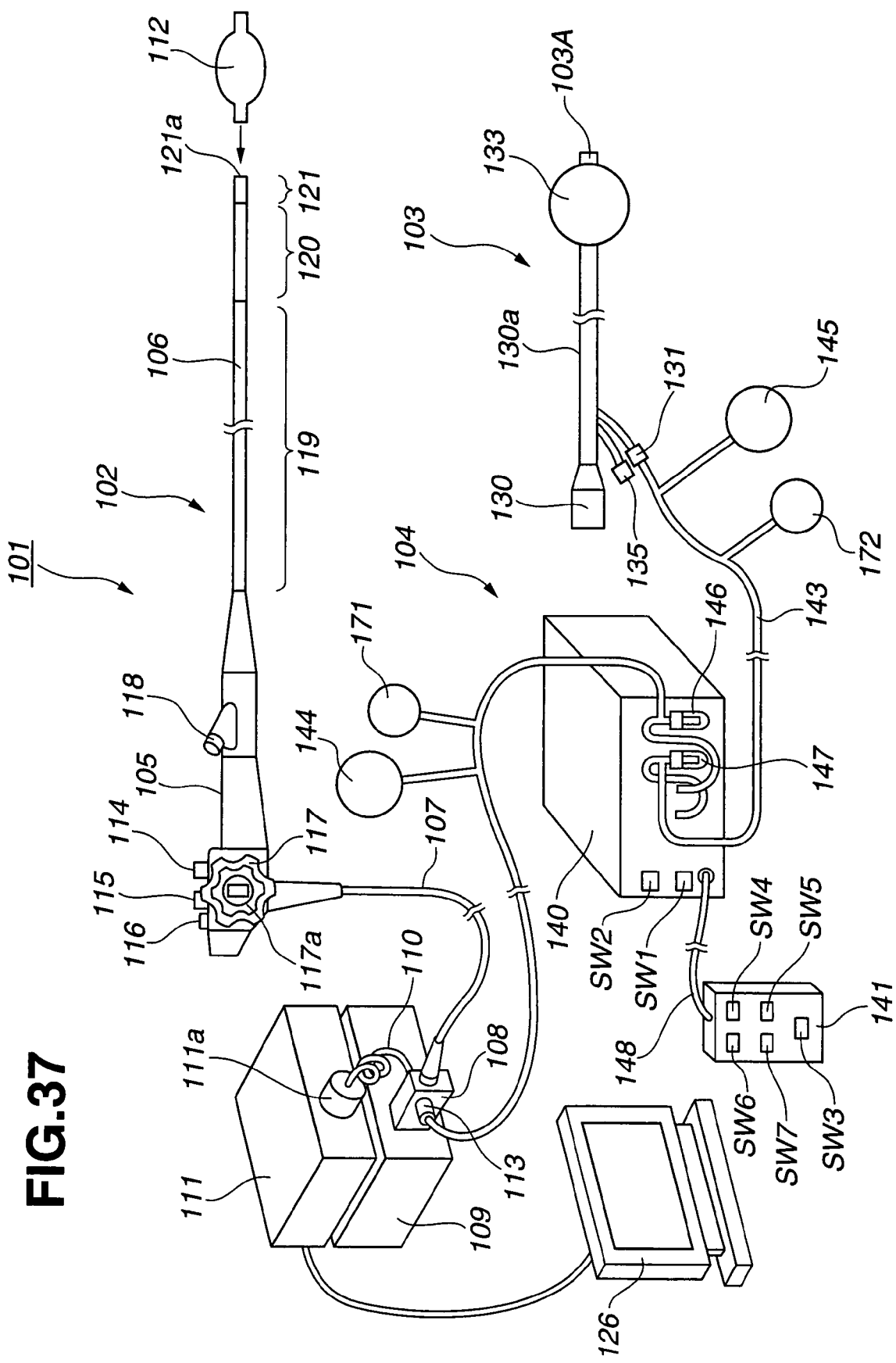
FIG. 37 is a system configuration diagram of an endoscope apparatus according to a fourth embodiment of the present invention.

Next, the fourth embodiment of the present invention will be described with reference to FIG. 37. FIG. 37 is a system configuration diagram of the endoscope apparatus according to the fourth embodiment of the present invention. In the description of the present embodiment, components that are the same as those of the endoscope apparatus according to the third embodiment are denoted by the same symbols and a description of those components is omitted, and only the portions that are different are described.

The endoscope apparatus 101 according to the present embodiment further comprises a fifth balloon 171 and a sixth balloon 172, and the remaining configuration is substantially the same as in the first embodiment.

As shown in FIG. 37, the fifth balloon 171 is provided so as to connect partway along the first tube 142 in the vicinity of the second balloon 144. Further, the sixth balloon 172 is provided so as to connect partway along the second tube 143 in the vicinity of the fourth balloon 145.

According to the present embodiment, the second and fourth balloons 144 and 145 are, for example, colored so as to become red or are formed using a red material, and the fifth and sixth balloons 171 and 172 are, for example, colored so as to become blue or are formed using a blue material, so that the respective balloons are color coded.

In this connection, color coding of the balloons is not limited to color coding by red or blue, and a configuration may be adopted in which color coding is performed by using multiple colors.

Since the fifth and sixth balloons 171 and 172 have the same configuration and the same functions, only the fifth balloon 171 will be described in the following description in order to simplify the description.

The present embodiment is configured such that an expansion starting pressure from a natural state (i.e. a state in which a balloon is neither expanded nor contracted) is, for example, 3 kpa for the first balloon 112, 10 kpa for the second balloon 144, and 5 kpa for the fifth balloon 171.

According to this configuration, in a state in which the pressure inside the supply line 161 (see FIG. 27) is 5 kpa or more and less than 10 kpa, although naturally the first balloon 112 expands, only the blue colored fifth balloon 171 among the identification balloons on the side near the technician's hands expands.

Further, when the pressure inside the supply line 161 (see FIG. 27) reaches 10 kpa or more, although naturally the first balloon 112 and the fifth balloon 171 expand, the red colored second balloon 144 that indicates an abnormally high pressure state also expands.

Accordingly, the technician can look at the respective expansion states of the blue fifth balloon 171 and the red second balloon 144 on the side near the technician's hands to easily ascertain whether the first balloon 112 inside the body cavity is in an appropriate state or is in an abnormally high pressure state.

The other configurations and actions are the same as in the first embodiment.

Accordingly, the same effect as in the first embodiment can be obtained according to the present embodiment.

Fifth Embodiment

Figure 38:
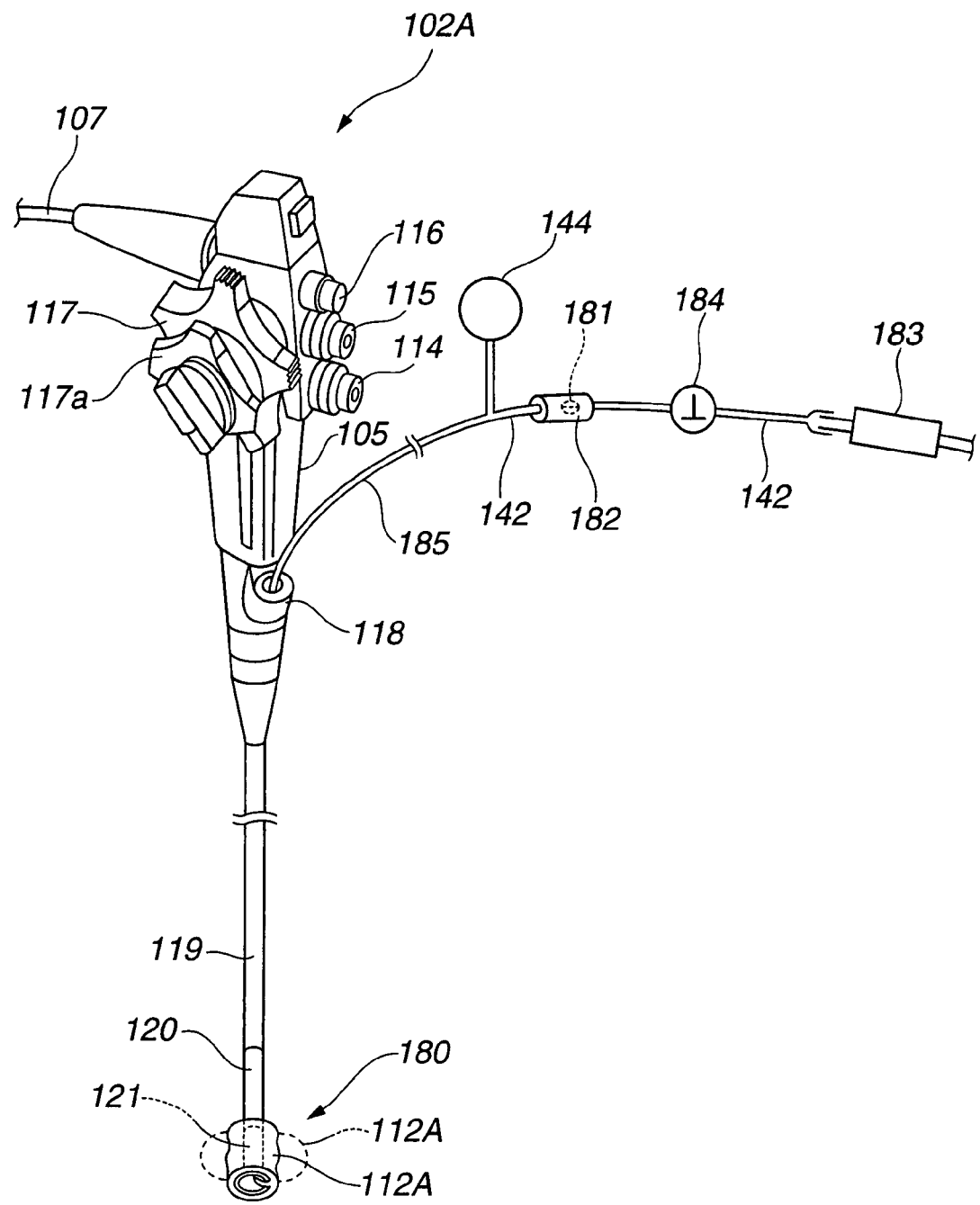
FIG. 38 is an oblique perspective view that shows the configuration of an endoscope provided with an endoscope insertion assisting device in an endoscope apparatus according to a fifth embodiment of the present invention.
Figure 39:
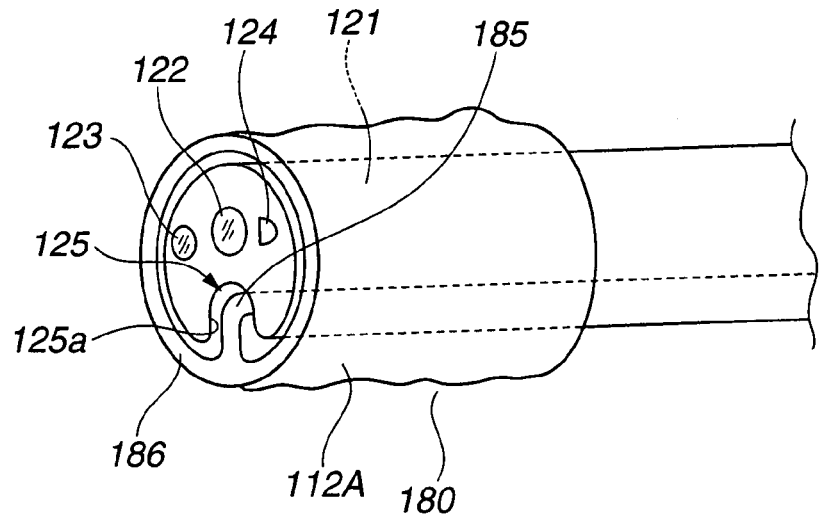
FIG. 39 is a magnified oblique perspective view that shows the configuration of the distal end of the endoscope shown in FIG. 38.
Figure 40:
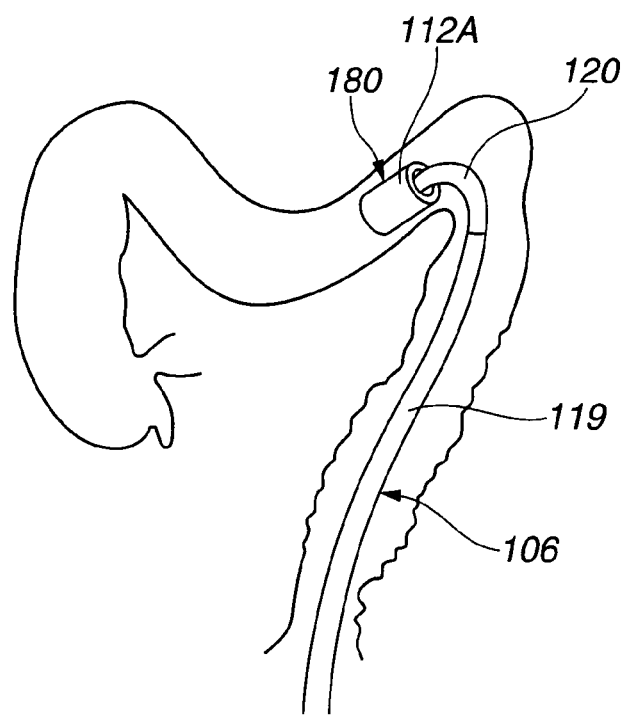
FIG. 40 is a view showing a state in which the insertion unit is inserted into the large intestine.
Figure 41:
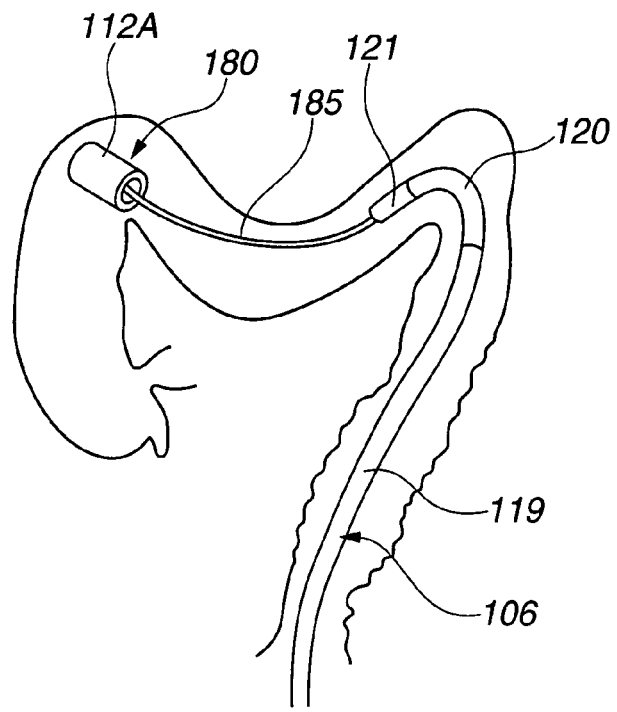
FIG. 41 is a view showing a state in which an endoscope insertion assisting device is fed toward the front of the field of view in the state shown in FIG. 40.
Figure 42:
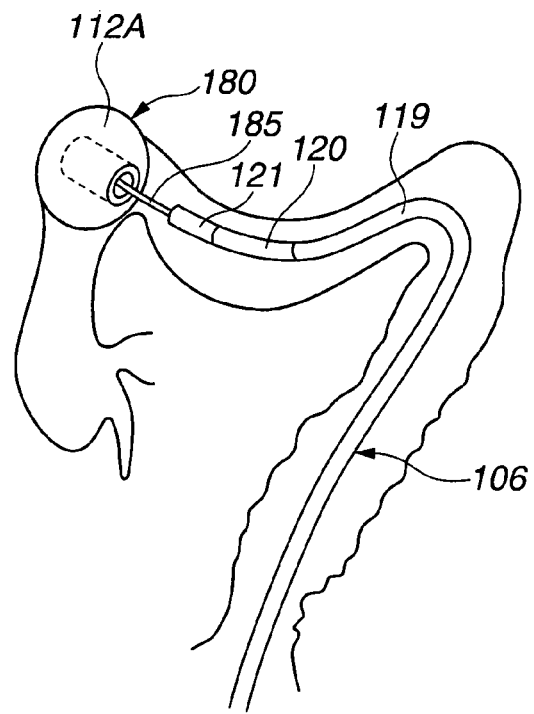
FIG. 42 is a view showing a state in which, from the state shown in FIG. 41, after expanding the first balloon using a syringe to retain the intestinal tract, the insertion unit is inserted into a deep part of the intestinal tract.

Next, the fifth embodiment of the present invention will be described with reference to FIGS. 38 to 42. FIGS. 38 to 42 relate to the fifth embodiment of the present invention. FIG. 38 is an oblique perspective view that shows the configuration of an endoscope mounted with an endoscope insertion assisting device in an endoscope apparatus. FIG. 39 is a magnified oblique perspective view that shows the configuration of the distal end of the endoscope shown in FIG. 38. FIGS. 40 to 42 are explanatory drawings for describing the action of the endoscope apparatus shown in FIG. 38. In the following description, components that are the same as those of the endoscope apparatus according to the third embodiment are denoted by the same symbols and a description of those components is omitted, and only the portions that are different are described.

In the endoscope apparatus 101 according to the present embodiment, the fifth balloon 171 is eliminated and an elastic member 182 is provided instead, and an endoscope insertion assisting device 180 having a first balloon 112A that corresponds to the first balloon 112 is also provided.

As shown in FIG. 38, the endoscope apparatus 101 has a substantially similar endoscope 102A. The endoscope 102A is provided with an endoscope insertion assisting device 180 having a first balloon 112A and an elastic member 182 and the like instead of the fifth balloon 171. In the example shown in FIG. 38, although a second balloon 144 is provided, a configuration may be adopted in which only the elastic member 182 is provided. The second balloon 144 constitutes a first elastic member and the elastic member 182 constitutes a second elastic member.

More specifically, since the elastic member 182 is provided in place of the fifth balloon 171 of the fourth embodiment, it is formed in a sheet shape using an elastic member that is made of rubber or the like. The elastic member 182 is adherently fixed so as to cover an opening hole 181 that opens on the first tube 142.

Further, according to the present embodiment, the balloon control device 104 is not provided, and as a substitute therefor a fluid such as air is supplied to the first balloon 112A by a manual operation using a syringe 183.

The syringe 183 is provided so as to communicate with the proximal portion of the first tube 142. In the vicinity of the syringe 183 is provided a stopcock portion 184 for performing a manual operation to open and close the conduit of the first tube 142.

Further, the first balloon 112A is not a component that is mounted and fixed on the endoscope 102 as in the third embodiment, and can be protruded forward of the field of view from the distal end 121 by an operation on the technician's side. The configuration of the endoscope insertion assisting device 180 having this kind of first balloon 112 is described later.

As shown in FIG. 38 and FIG. 39, the endoscope insertion assisting device 180 mainly comprises the first balloon 112A, a balloon retaining member 186 that retains the first balloon 112A, and a shaft 185.

The aforementioned first balloon 112A is mounted so as to sheathe the distal end 121 of the insertion unit 106. The shaft 185 constitutes a supply and exhaust line that allows the passage of a fluid such as air for expanding/contracting the first balloon 112A, and also moves the first balloon 112A and a balloon retaining member 186 forward or backward.

The endoscope insertion assisting device 180 may be a disposable article that is discarded after one use, or may be a reusable article that is reused after being washed, disinfected and sterilized after use.

The balloon retaining member 186 is connected and fixed to the distal end of the shaft 185 by an unshown connecting member. The balloon retaining member 186 adherently fixes and retains the first balloon 112A so as to be covered by the first balloon 112A.

The balloon retaining member 186 is formed in a hollow shape such that it can cover the distal end 121 of the endoscope 102 from the distal side, and is formed using a resin member that has electrical insulation properties, for example, a fluorocarbon resin such as Teflon®.

The shaft 185 comprises a member that has flexibility. Inside the shaft 185 is provided a supply and exhaust line (not shown) for supplying and exhausting air to and from the inside of the first balloon 112A. The proximal portion of the shaft 185 is connected in a communicating manner to the first tube 142.

Accordingly, when supplying or exhausting air by a manual operation using the syringe 183, the first balloon 112A can be expanded or contracted by supplying or exhausting the air to or from the inside of the first balloon 112A through the supply and exhaust line (not shown) inside the shaft 185. In this connection, the chain double-dashed line shown in FIG. 38 shows one example of the expansion state of the first balloon 112A.

The first balloon 112A is retained so as to sheathe the outside of the hollow-shaped balloon retaining member 186, and the two sides thereof are hermetically fixed. The supply and exhaust line (not shown) inside the shaft 185 is provided so as to communicate (not shown) with the inside of the first balloon 112A.

Further, as shown in FIG. 39, the channel opening 125 that forms an opening of a channel 125a that is provided inside the insertion unit 106 is disposed, for example, in a substantially orthogonal manner to a side linking the air supply and water supply nozzle 124, the objective lens 122 and the illumination lens 123 in one direction.

The channel opening 125 opens from the front surface of the distal end 121 to the side surface thereof. The shaft 185 that comprises the endoscope insertion assisting device 180 passes through the channel opening 125.

The endoscope 102A shown in FIG. 38 represents a state before insertion into a body cavity. More specifically, according to the present embodiment, the shaft 185 comprising the endoscope insertion assisting device 180 is inserted from the channel opening 125 side of the distal end 121 and guided to outside through the forceps insertion port 118 of the operation unit 105.

Thus, according to this configuration, by grasping a portion of the shaft 185 that extends from the forceps insertion port 118 of the operation unit 105 and performing an operation to advance or retreat the shaft 185, the technician can freely position the first balloon 112A that is provided at the tip of the endoscope insertion assisting device 180 forward or rearward of the field of view.

The remaining configuration is the same as that of the third embodiment.

Next, the action of the endoscope apparatus according to the present embodiment will be described with reference to FIGS. 40 to 42. FIG. 40 is a view showing a state in which the insertion unit is inserted into the large intestine. FIG. 41 is a view showing a state in which the endoscope insertion assisting device is fed to the front of the field of view in the state shown in FIG. 40. FIG. 42 is a view showing a state in which, from the state shown in FIG. 41, after expanding the first balloon using the syringe to retain the intestinal tract, the insertion unit is inserted into a deep part.

As shown in FIG. 40, in a case in which, for example, the distal end 121 of the endoscope 102 is at a splenic curvature when the insertion unit 106 is being inserted into the large intestine by the technician, even when the technician pushes in the insertion unit 106 in an attempt to push the distal end 121 further forward, because the intestinal tract is soft and is not immobilized and because the direction in which the technician pushes in the insertion unit 106 is different to the direction in which the technician wants the distal end 121 of the insertion unit 106 to advance, a state may arise in which it is extremely difficult to advance the insertion unit 106.

To bypass this situation, as shown in FIG. 41, the technician advances or pulls back the shaft 185 to feed the first balloon 112A forward of the field of view. In this case, since the shaft 185 can be utilized as an insertion guide, it is possible to, for example, advance the first balloon 112A to the back of the hepatic curvature as shown in FIG. 41.

Next, as shown in FIG. 42, the technician expands the first balloon 112A from the state shown in FIG. 41 using the syringe 183, and after retaining the intestinal tract, performs an insertion operation to advance the distal end 121 of the insertion unit 106 into a deep part employing the shaft 185 as an insertion guide.

When it is difficult to insert the distal end 121 of the insertion unit 106 into the back part, by repeating the above-described series of operations the technician can insert the distal end 121 of the insertion unit 106 into the deep part of the lumen.

In this connection, since the insertion unit 106 is configured to be loaded from the tip, and not to be passed through from the side of the technician's hands, the first balloon 112A can be mounted as a large-size balloon member that has a large intestinal tract immobilizing force. Thus, by mounting a large-size first balloon 112A, the intestinal tract immobilizing force can be increased.

The elastic member 182 having the same function as in the third embodiment is provided on the first tube 142. Therefore, similarly to the third embodiment, since the elastic member 182 expands by the corresponding amount when the first balloon 112A is restricted from outside by contact with a body wall or the like, a function as a safety device whereby the excessive pressure within the first balloon 112A is simply and quickly released is also obtained. Thus, by viewing the state of the elastic member 182, the technician can be aware of the state of the first balloon 112A that is inserted into the body cavity.

The other actions are the same as in the third embodiment.

Thus, according to the present embodiment, it is possible to recognize the supply and exhaust state of air with respect to the first balloon 112 that was inserted into a body cavity, using a simple configuration and at a low cost. The other effects are the same as the third embodiment.

In the present embodiment, the endoscope 102A shown in FIG. 38 may also be configured using a double balloon system that combines the balloon-attached overtube 103 shown in FIG. 22, and these combinations shall not particularly be limited by the purport of the present invention.

The endoscope apparatus 101 of the present invention can also be implemented by a first and second modification examples described hereafter. The first and second modification examples will be described with reference to FIG. 43 to FIG. 47.

Figure 43:
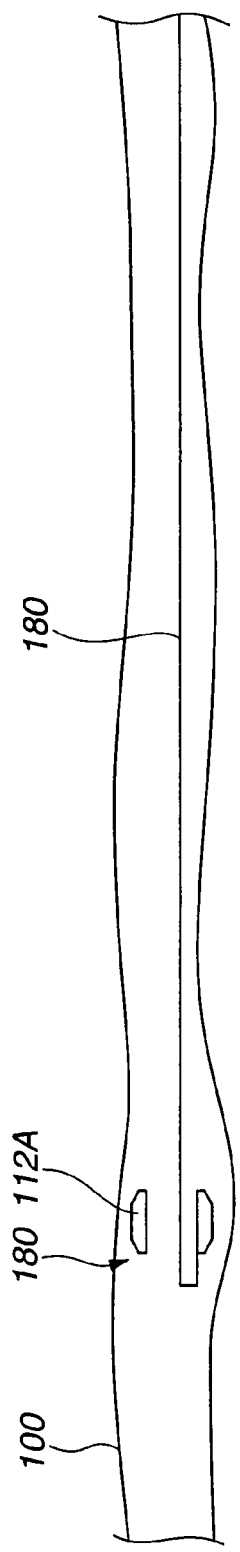
FIG. 43 is a view illustrating a first modification example of the fifth embodiment, and shows a state in which an endoscope insertion assisting device that was swallowed orally is inserted into a deep part of the intestinal tract.
Figure 44:
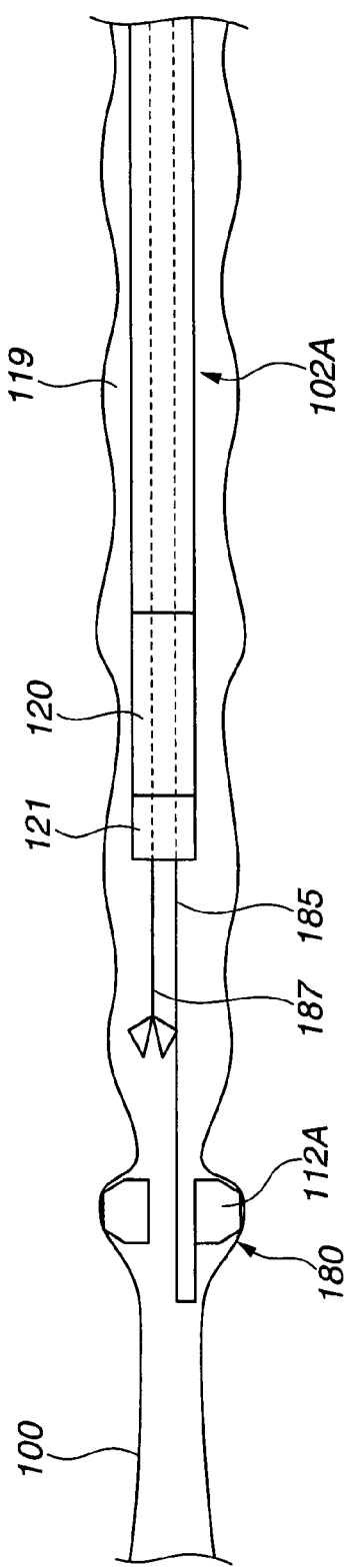
FIG. 44 is a view showing a state in which treatment is carried out using a treatment instrument while expanding a first balloon to retain the intestinal tract.

FIG. 43 and FIG. 44 illustrate a first modification example of the present embodiment, and are provided for describing another operating method of the endoscope insertion assisting device. FIG. 43 is a view that shows a state in which an endoscope insertion assisting device that was swallowed orally is inserted into a deep part of the intestinal tract. FIG. 44 is a view showing a state in which treatment is carried out using a treatment instrument while expanding a first balloon to retain the intestinal tract.

As shown in FIG. 43, a technician causes a patient to swallow orally the endoscope insertion assisting device 180 and then, utilizing the peristaltic advance/retreat of the gastrointestinal tract, inserts the endoscope insertion assisting device 180 into a deep part of the intestinal tract 100.

Next, as shown in FIG. 44, the technician expands the first balloon 112A to retain the intestinal tract 100, and then inserts the insertion unit 106 of the endoscope 102A using the shaft 185 as an insertion guide.

In this case, by using an endoscope equipped with, for example, two channels as the endoscope 102A, since a treatment channel that can allow a treatment instrument to pass therethrough is internally provided in addition to the channel 125a through which the shaft 185 shown in FIG. 38 passes, after inserting the endoscope 102A into a deep part while sliding it along the shaft 185, it is possible to insert a treatment instrument 187 to perform various kinds of treatment or therapy.

Further, when inserting the endoscope insertion assisting device 180 into a deep part of the intestinal tract 100 utilizing peristaltic advance/retreat, since the expansion amount (diameter) of the first balloon 112A can be changed in accordance with the patient or site, it is possible to utilize the peristaltic advance/retreat more effectively, and to also insert the first balloon 112A into a deep part of the intestinal tract 100 in a short time.

A method of using the endoscope insertion assisting device 180 is not limited to the usage method illustrated in the present embodiment and the modification example, and the endoscope insertion assisting device 180 may be operated using a usage method other than these.

FIG. 45 to FIG. 47 illustrate a second modification example of the present embodiment, and describe an operating method using an endoscope insertion assisting device that incorporated a capsule endoscope. FIG. 45 is a view illustrating a state in which a first balloon is inserted into a deep part of the intestinal tract while performing observation with a capsule endoscope. FIG. 46 is a view showing a state in which the first balloon is expanded from the state shown in FIG. 45 to insert an endoscope, and a treatment instrument is further inserted. FIG. 47 is a view showing a state in which, after completing treatment at the deep part of the intestinal tract, the endoscope is withdrawn to recover the capsule endoscope.

As shown in FIG. 45, an endoscope insertion assisting device 180a is configured to incorporate a capsule endoscope 188 at the inner side of the first balloon 112A. As shown in FIG. 45, the technician inserts the first balloon 112A into a deep part of the intestinal tract 100 while observing the inside of the intestinal tract 100 with the capsule endoscope 188. In this case, the technician can perform observation by viewing an endoscope image that is captured in the field of view range θ of the capsule endoscope 188.

Next, as shown in FIG. 46, the technician expands the first balloon 112A from the state shown in FIG. 45 and inserts the endoscope 102A into a deep part while employing the shaft 185 as an insertion guide. Thereafter, the technician inserts the treatment instrument 187 through the treatment instrument insertion channel of the endoscope 102A, to cause it to protrude to the side forward of the distal end 121. As a result, the technician can perform various kinds of treatment or therapy.

After performing treatment or therapy at the deep part of the intestinal tract 100, as shown in FIG. 47, the technician withdraws the endoscope 102A to recover the capsule endoscope 188. The recovered capsule endoscope 188 can be reused.

In the second modification example, by adopting a configuration in which the first balloon 112A is expanded somewhat according to the patient or site to reach a size that is suitable to the peristaltic advance/retreat, the capsule endoscope 188 can be advanced to a deep part in a shorter time.

Further, since the first balloon 112A and the shaft 185 are linked together, it is possible to always advance the capsule endoscope 188 towards the anus and perform observation as far as a deep part while securing a stable field of view.

The invention described in the foregoing embodiments is not limited to those embodiments and modification examples, and various changes and modifications and the like are possible at the implementation stage without deviating from the spirit and scope of the present invention. Further, the embodiments include inventions of various stages, and various inventions can be extracted by appropriately combining a plurality of the disclosed configuration requirements.

For example, if a problem described herein as a problem to be overcome by the invention can be solved and if the effects described herein are still obtained after omitting some of the configuration requirements shown in the embodiments, then the configuration obtained by omitting the configuration requirements can be extracted as an embodiment of the invention.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An endoscope insertion assisting device, comprising:
   a balloon retaining member having a hollow shape to cover a distal end of an insertion portion of an endoscope from a distal side of the insertion portion;
   a first balloon member retained by the balloon retaining member and into which the insertion portion of the endoscope is inserted, the first balloon member having a first hollow portion;
   a first transmission member that includes, at a distal end part thereof, a curved portion curved outward in a radial direction of the insertion portion of the endoscope inside the hollow shape of the balloon retaining member, wherein the first balloon member is provided at the distal end part from the curved portion toward a proximal end side of the first transmission member, the first transmission member being adapted to be passed through a channel of the insertion portion of the endoscope and transmit an advance/retreat action performed by an operator to the first balloon member to move the first balloon member to a side distal to a distal end of the insertion portion of the endoscope;
   a second balloon member into which the insertion portion of the endoscope is inserted, the second balloon member having a second hollow portion;
   a tubular light-transmissive second transmission member, wherein the second balloon member is provided at a distal end part thereof, the second transmission member being adapted to allow the insertion portion of the endoscope to pass therethrough and transmit an advance/retreat action performed by an operator to the second balloon member to move the second balloon member slidingly along the insertion portion of the endoscope; and
   a control portion that controls supply and exhaust of fluid to and from inside of the first hollow portion of the first balloon member and the second hollow portion of the second balloon member to expand or contract the first balloon member and the second balloon member,
   wherein the distal end of the insertion portion of the endoscope comes into contact with the curved portion of the first transmission member, which regulates a movement of the insertion portion of the endoscope distal to the curved portion.

2. The endoscope insertion assisting device according to claim 1, wherein the control portion comprises:
   a first fluid supply and exhaust portion comprising a conduit that is connected to the first balloon member and expands or contracts the first balloon member by supplying or exhausting a fluid to or from inside of the first hollow portion; and a second fluid supply and exhaust portion comprising a conduit that is connected to the second balloon member and expands or contracts the second balloon member by supplying or exhausting a fluid to or from inside of the second hollow portion.

3. The endoscope insertion assisting device according to claim 1, wherein,
the first transmission member has a first operation unit for operating the first transmission member; and
the second transmission member has a second operation unit for operating the second transmission member.

4. The endoscope insertion assisting device according to claim 2, wherein,
the first transmission member has a first operation unit for operating the first transmission member; and
the second transmission member has a second operation unit for operating the second transmission member.

5. The endoscope insertion assisting device according to claim 1, wherein an endoscope that is equipped with the insertion portion of the endoscope that observes, in a condition in which the insertion portion of the endoscope can advance or retreat, inside of a lumen that is retained by the first balloon member and the second balloon member is constituted in combination with both the first balloon member and the second balloon member.

6. The endoscope insertion assisting device according to claim 1, wherein the first transmission member is configured as a shaft member which has elasticity or flexibility such that the shaft member can bend accompanying a bending operation of a bending portion that is provided in the insertion portion of the endoscope.

7. An endoscope apparatus, comprising:
an endoscope comprising a long and slender insertion portion that is insertable into a body cavity, and
an endoscope insertion assisting device that is constituted in combination with the endoscope;
wherein, the endoscope insertion assisting device comprises:
a balloon retaining member having a hollow shape to cover a distal end of an insertion portion of an endoscope from a distal side of the insertion portion;
a first balloon member retained by the balloon retaining member and into which the insertion portion of the endoscope is inserted, the first balloon member having a first hollow portion;
a first transmission member that includes, at a distal end part thereof, a curved portion curved outward in a radial direction of the insertion portion of the endoscope inside the hollow shape of the balloon retaining member, wherein the first balloon member is provided at the distal end part from the curved portion toward a proximal end side of the first transmission member, the first transmission member being adapted to be passed through a channel of the insertion portion of the endoscope and transmit an advance/retreat action performed by an operator to the first balloon member to move the first balloon member to a side distal to a distal end of the insertion portion of the endoscope;
a second balloon member into which the insertion portion of the endoscope is inserted, the second balloon member having a second hollow portion;
a tubular light-transmissive second transmission member wherein the second balloon member is provided at a distal end part thereof, the second transmission member being adapted to allow the insertion portion of the endoscope to pass therethrough and transmit an advance/retreat action performed by an operator to the second balloon member to move the second balloon member slidingly along the insertion portion of the endoscope; and
a control portion that controls supply and exhaust of fluid to and from inside of the first hollow portion of the first balloon member and the second hollow portion of the second balloon member to expand or contract the first balloon member and the second balloon member,
wherein the distal end of the insertion portion of the endoscope comes into contact with the curved portion of the first transmission member, which regulates a movement of the insertion portion distal to the curved portion.

* * * * *